US008905916B2

(12) United States Patent
Jacobs et al.

(10) Patent No.: US 8,905,916 B2
(45) Date of Patent: Dec. 9, 2014

(54) IMPLANTABLE ACCESS PORT SYSTEM

(71) Applicant: Apollo Endosurgery, Inc., Austin, TX (US)

(72) Inventors: Jordan Jacobs, Randolph, MA (US); Mark Orphanos, Stoughton, MA (US); Chris Maurer, Wakefield, MA (US); Kenneth A. Eliasen, Wrentham, MA (US); Matthew B. Denardo, West Roxbury, MA (US)

(73) Assignee: Apollo Endosurgery, Inc., Austin, TX (US)

( * ) Notice: Subject to any disclaimer, the term of this patent is extended or adjusted under 35 U.S.C. 154(b) by 0 days.

(21) Appl. No.: 13/922,123

(22) Filed: Jun. 19, 2013

(65) Prior Publication Data

US 2013/0281769 A1    Oct. 24, 2013

Related U.S. Application Data

(63) Continuation of application No. 12/857,447, filed on Aug. 16, 2010, now abandoned.

(51) Int. Cl.
*A61F 2/00* (2006.01)
*A61F 2/04* (2013.01)
*A61M 39/02* (2006.01)
*A61F 5/00* (2006.01)

(52) U.S. Cl.
CPC .............. *A61F 2/04* (2013.01); *A61M 39/0208* (2013.01); *A61M 2039/0223* (2013.01); *A61F 5/0056* (2013.01)
USPC .......................................................... 600/37

(58) Field of Classification Search
USPC ...................... 600/37; 606/139, 151
See application file for complete search history.

(56) References Cited

U.S. PATENT DOCUMENTS

| 586,113 A | 7/1897 | Bott |
| 2,163,048 A | 6/1939 | McKee |

(Continued)

FOREIGN PATENT DOCUMENTS

| EP | 0343910 A2 | 11/1989 |
| EP | 0611561 | 8/1994 |

(Continued)

OTHER PUBLICATIONS http://en.wikipedia.org/wiki/Injection.sub.—molding, Mar. 20, 2014.

(Continued)

*Primary Examiner* — Jacqueline Cheng
*Assistant Examiner* — Kaylee Wilson
(74) *Attorney, Agent, or Firm* — Gordon & Jacobson, PC

(57) ABSTRACT

An implantable injection port for use with a gastric band for treating obesity and for attaching to a tissue of a patient is disclosed. The implantable injection port includes a base having an anchor opening, a gear coupled to the base and rotatable about a central axis, the gear having a plurality of gear teeth, an anchor coupled to the gear, and a top portion spaced apart from the base and having a plurality of top teeth that engage with the plurality of gear teeth. The top portion is rotatable causing rotation of the gear such that the rotation of the gear causes movement of the anchor through the anchor opening of the base and into the tissue of the patient.

21 Claims, 14 Drawing Sheets

(56) References Cited

U.S. PATENT DOCUMENTS

| | | |
|---|---|---|
| 2,737,954 A | 3/1956 | Knapp |
| 3,371,352 A | 3/1968 | Siposs |
| 3,569,660 A | 3/1971 | Houldcroft |
| 3,587,115 A | 6/1971 | Shiley |
| 3,596,660 A | 8/1971 | Melone |
| 3,667,081 A | 6/1972 | Burger |
| 3,688,764 A | 9/1972 | Reed |
| 3,731,352 A | 5/1973 | Okamoto |
| 3,840,018 A | 10/1974 | Heifetz |
| 3,958,562 A | 5/1976 | Hakim |
| 3,971,376 A | 7/1976 | Wichterle |
| 4,019,499 A | 4/1977 | Fitzgerald |
| 4,118,805 A | 10/1978 | Reimels |
| 4,151,835 A | 5/1979 | Copeland |
| 4,161,943 A | 7/1979 | Nogier |
| 4,164,943 A | 8/1979 | Hill |
| 4,190,040 A | 2/1980 | Schulte |
| 4,233,992 A | 11/1980 | Bisping |
| 4,265,252 A | 5/1981 | Chubbuck |
| 4,280,722 A | 7/1981 | Guptil |
| 4,413,985 A | 11/1983 | Wellner |
| 4,474,572 A | 10/1984 | McNaughton |
| 4,502,335 A | 3/1985 | Wamstad |
| 4,543,088 A | 9/1985 | Bootman |
| 4,557,722 A | 12/1985 | Harris |
| 4,569,675 A | 2/1986 | Prosl |
| 4,588,394 A | 5/1986 | Schulte |
| 4,592,339 A | 6/1986 | Kuzmak |
| 4,592,355 A | 6/1986 | Antebi |
| 4,634,427 A | 1/1987 | Hannula |
| 4,655,765 A | 4/1987 | Swift |
| 4,673,394 A | 6/1987 | Fenton |
| 4,692,146 A | 9/1987 | Hilger |
| 4,696,288 A | 9/1987 | Kuzmak |
| 4,704,103 A | 11/1987 | Stoeber |
| 4,710,174 A | 12/1987 | Moden |
| 4,738,657 A | 4/1988 | Hancock |
| 4,767,410 A | 8/1988 | Moden |
| 4,772,270 A | 9/1988 | Wiita |
| 4,778,452 A | 10/1988 | Moden |
| 4,781,680 A | 11/1988 | Redmond |
| 4,796,641 A | 1/1989 | Mills |
| 4,802,885 A | 2/1989 | Weeks |
| 4,832,054 A | 5/1989 | Bark |
| 4,840,615 A | 6/1989 | Hancock |
| 4,850,227 A | 7/1989 | Luettgen |
| 4,858,623 A | 8/1989 | Bradshaw |
| 4,861,341 A | 8/1989 | Woodburn |
| 4,881,939 A | 11/1989 | Newman |
| 4,886,501 A | 12/1989 | Johnston |
| 4,902,278 A | 2/1990 | Maget |
| 4,904,241 A | 2/1990 | Bark |
| 4,913,702 A | 4/1990 | Yum |
| 4,915,690 A | 4/1990 | Cone |
| 4,929,230 A | 5/1990 | Pfleger |
| 4,929,236 A | 5/1990 | Sampson |
| 4,966,588 A | 10/1990 | Rayman |
| 4,967,755 A | 11/1990 | Pohndorf |
| 4,978,338 A | 12/1990 | Melsky |
| 5,006,115 A | 4/1991 | McDonald |
| 5,013,298 A | 5/1991 | Moden |
| 5,026,344 A | 6/1991 | Dijkstra |
| 5,041,098 A | 8/1991 | Loiterman |
| 5,045,060 A | 9/1991 | Melsky |
| 5,074,868 A | 12/1991 | Kuzmak |
| 5,090,954 A | 2/1992 | Geary |
| 5,092,897 A | 3/1992 | Forte |
| 5,094,244 A | 3/1992 | Callahan |
| 5,108,377 A | 4/1992 | Cone |
| 5,125,408 A | 6/1992 | Basser |
| 5,133,753 A | 7/1992 | Bark |
| 5,137,529 A | 8/1992 | Watson |
| 5,147,483 A | 9/1992 | Melsky |
| 5,152,747 A | 10/1992 | Olivier |
| 5,167,638 A | 12/1992 | Felix |
| 5,185,003 A | 2/1993 | Brethauer |
| 5,207,644 A | 5/1993 | Strecker |
| 5,213,574 A | 5/1993 | Tucker |
| 5,226,429 A | 7/1993 | Kuzmak |
| 5,226,894 A | 7/1993 | Haber |
| 5,250,026 A | 10/1993 | Ehrlich |
| 5,273,537 A | 12/1993 | Haskvitz |
| 5,281,205 A | 1/1994 | McPherson |
| 5,284,479 A | 2/1994 | De Jong |
| 5,318,545 A | 6/1994 | Tucker |
| 5,336,194 A | 8/1994 | Polaschegg |
| 5,337,747 A | 8/1994 | Neftel |
| 5,360,407 A | 11/1994 | Leonard |
| 5,368,040 A | 11/1994 | Carney |
| 5,387,192 A | 2/1995 | Glantz |
| 5,391,164 A | 2/1995 | Giampapa |
| 5,449,368 A | 9/1995 | Kuzmak |
| 5,476,460 A | 12/1995 | Montalvo |
| 5,514,174 A | 5/1996 | Heil |
| 5,540,648 A | 7/1996 | Yoon |
| 5,556,388 A | 9/1996 | Johlin |
| 5,558,641 A | 9/1996 | Glantz |
| 5,562,617 A | 10/1996 | Finch |
| 5,571,104 A | 11/1996 | Li |
| 5,575,777 A | 11/1996 | Cover |
| 5,601,604 A | 2/1997 | Vincent |
| 5,637,102 A | 6/1997 | Tolkoff |
| 5,653,755 A | 8/1997 | Ledergerber |
| 5,658,298 A | 8/1997 | Vincent |
| 5,674,397 A | 10/1997 | Pawlak |
| 5,683,447 A | 11/1997 | Bush |
| 5,688,237 A | 11/1997 | Rozga |
| 5,695,490 A | 12/1997 | Flaherty |
| 5,716,342 A | 2/1998 | Dumbraveanu |
| 5,718,682 A | 2/1998 | Tucker |
| 5,722,957 A | 3/1998 | Steinbach |
| 5,748,200 A | 5/1998 | Funahashi |
| 5,810,735 A | 9/1998 | Halperin |
| 5,814,019 A | 9/1998 | Steinbach |
| 5,833,654 A | 11/1998 | Powers |
| 5,843,033 A | 12/1998 | Ropiak |
| RE36,176 E | 3/1999 | Kuzmak |
| 5,883,654 A | 3/1999 | Katsuyama |
| 5,902,598 A | 5/1999 | Chen |
| 5,906,596 A | 5/1999 | Tallarida |
| 5,910,149 A | 6/1999 | Kuzmak |
| 5,911,704 A | 6/1999 | Humes |
| 5,931,829 A | 8/1999 | Burbank |
| 5,932,460 A | 8/1999 | Mills |
| 5,935,083 A | 8/1999 | Williams |
| 5,938,669 A | 8/1999 | Klaiber |
| 5,951,512 A | 9/1999 | Dalton |
| 6,024,704 A | 2/2000 | Meador |
| 6,030,369 A | 2/2000 | Engelson |
| 6,039,712 A | 3/2000 | Fogarty |
| 6,074,341 A | 6/2000 | Anderson |
| 6,090,066 A | 7/2000 | Schnell |
| 6,098,405 A | 8/2000 | Miyata |
| 6,102,678 A | 8/2000 | Peclat |
| 6,102,922 A | 8/2000 | Jakobsson |
| 6,123,700 A | 9/2000 | Mills |
| 6,152,885 A | 11/2000 | Taepke |
| 6,171,252 B1 | 1/2001 | Roberts |
| 6,183,449 B1 | 2/2001 | Sibbitt |
| 6,213,973 B1 | 4/2001 | Eliasen |
| 6,221,024 B1 | 4/2001 | Miesel |
| 6,234,973 B1 | 5/2001 | Meador |
| 6,258,079 B1 | 7/2001 | Burbank |
| 6,264,676 B1 | 7/2001 | Gellman |
| 6,270,475 B1 | 8/2001 | Bestetti |
| 6,283,949 B1 | 9/2001 | Roorda |
| 6,321,124 B1 | 11/2001 | Cigaina |
| 6,349,740 B1 | 2/2002 | Cho |
| 6,432,040 B1 | 8/2002 | Meah |
| 6,450,946 B1 | 9/2002 | Forsell |
| 6,453,907 B1 | 9/2002 | Forsell |
| 6,454,699 B1 | 9/2002 | Forsell |
| 6,459,917 B1 | 10/2002 | Gowda |
| 6,461,293 B1 | 10/2002 | Forsell |

(56) References Cited

U.S. PATENT DOCUMENTS

| | | |
|---|---|---|
| 6,464,628 B1 | 10/2002 | Forsell |
| 6,470,213 B1 | 10/2002 | Alley |
| 6,470,892 B1 | 10/2002 | Forsell |
| 6,478,783 B1 | 11/2002 | Moorehead |
| 6,511,490 B2 | 1/2003 | Robert |
| 6,547,801 B1 | 4/2003 | Dargent |
| 6,572,587 B2 | 6/2003 | Lerman |
| 6,589,184 B2 | 7/2003 | Noren |
| 6,648,849 B2 | 11/2003 | Tenhuisen |
| 6,666,845 B2 | 12/2003 | Hooper |
| 6,689,100 B2 | 2/2004 | Connelly |
| 6,723,053 B2 | 4/2004 | Ackerman |
| 6,733,519 B2 | 5/2004 | Lashinski |
| 6,792,309 B1 | 9/2004 | Noren |
| 6,810,880 B1 | 11/2004 | Jennings |
| 6,813,964 B1 | 11/2004 | Clark |
| 6,860,857 B2 | 3/2005 | Noren |
| 6,915,162 B2 | 7/2005 | Noren et al. |
| 6,921,267 B2 | 7/2005 | Van Oostrom |
| 6,929,631 B1 | 8/2005 | Brugger |
| 6,939,299 B1 | 9/2005 | Petersen |
| 6,953,444 B2 | 10/2005 | Rosenberg |
| 6,964,204 B2 | 11/2005 | Clark |
| 6,966,875 B1 | 11/2005 | Longobardi |
| 6,997,914 B2 | 2/2006 | Smith |
| 7,017,583 B2 | 3/2006 | Forsell |
| 7,020,531 B1 | 3/2006 | Colliou |
| 7,056,286 B2 | 6/2006 | Ravenscroft |
| 7,063,669 B2 | 6/2006 | Brawner |
| 7,073,387 B2 | 7/2006 | Zdeblick |
| 7,082,843 B2 | 8/2006 | Clark |
| 7,131,945 B2 | 11/2006 | Fink |
| 7,144,400 B2 | 12/2006 | Byrum |
| 7,149,587 B2 | 12/2006 | Wardle |
| 7,191,007 B2 | 3/2007 | Desai |
| 7,195,774 B2 | 3/2007 | Carvalho |
| 7,223,239 B2 | 5/2007 | Schulze |
| 7,226,419 B2 | 6/2007 | Lane |
| 7,261,003 B2 | 8/2007 | McDonald |
| 7,267,645 B2 | 9/2007 | Anderson |
| 7,282,023 B2 | 10/2007 | Frering |
| 7,311,716 B2 | 12/2007 | Byrum |
| 7,311,717 B2 | 12/2007 | Egle |
| 7,351,198 B2 | 4/2008 | Byrum |
| 7,351,226 B1 | 4/2008 | Herskowitz |
| 7,351,240 B2 | 4/2008 | Hassler |
| 7,353,747 B2 | 4/2008 | Swayze |
| 7,364,542 B2 | 4/2008 | Jambor |
| 7,367,937 B2 | 5/2008 | Jambor |
| 7,374,557 B2 | 5/2008 | Conlon |
| 7,374,565 B2 | 5/2008 | Hassler |
| 7,390,294 B2 | 6/2008 | Hassler |
| 7,413,547 B1 | 8/2008 | Lichtscheidl |
| 7,416,528 B2 | 8/2008 | Crawford |
| 7,437,951 B2 | 10/2008 | McDonald |
| 7,438,718 B2 | 10/2008 | Milliman |
| 7,445,614 B2 | 11/2008 | Bunodiere |
| 7,468,038 B2 | 12/2008 | Ye |
| 7,500,944 B2 | 3/2009 | Byrum |
| 7,510,530 B2 | 3/2009 | Hashimoto |
| 7,530,943 B2 | 5/2009 | Lechner |
| 7,553,298 B2 | 6/2009 | Hunt |
| 7,561,916 B2 | 7/2009 | Hunt |
| 7,580,746 B2 | 8/2009 | Gilkerson |
| 7,591,185 B1 | 9/2009 | Mothilal |
| 7,593,777 B2 | 9/2009 | Gerber |
| 7,634,319 B2 | 12/2009 | Schneider |
| 7,651,483 B2 | 1/2010 | Byrum |
| 7,658,196 B2 | 2/2010 | Ferreri |
| 7,699,770 B2 | 4/2010 | Hassler |
| 7,708,722 B2 | 5/2010 | Glenn |
| 7,762,998 B2 | 7/2010 | Birk |
| 7,762,999 B2 | 7/2010 | Byrum |
| 7,775,215 B2 | 8/2010 | Hassler |
| 7,775,966 B2 | 8/2010 | Dlugos |
| 7,811,275 B2 | 10/2010 | Birk |
| 7,850,660 B2 | 12/2010 | Uth |
| 7,862,546 B2 | 1/2011 | Conlon |
| 7,909,754 B2 | 3/2011 | Hassler |
| 7,909,804 B2 | 3/2011 | Stats |
| 8,007,474 B2 | 8/2011 | Uth |
| 2001/0052141 A1 | 12/2001 | Andersen |
| 2002/0013545 A1 | 1/2002 | Soltanpour |
| 2002/0058969 A1 | 5/2002 | Noren |
| 2002/0087147 A1 | 7/2002 | Hooper |
| 2002/0095181 A1 | 7/2002 | Beyar |
| 2002/0139208 A1 | 10/2002 | Yatskov |
| 2002/0198548 A1 | 12/2002 | Robert |
| 2003/0045800 A1 | 3/2003 | Noren |
| 2003/0045910 A1 | 3/2003 | Sorensen |
| 2003/0073880 A1 | 4/2003 | Polsky |
| 2003/0078506 A1 | 4/2003 | Noren |
| 2003/0139690 A1 | 7/2003 | Aebli |
| 2004/0064110 A1 | 4/2004 | Forsell |
| 2004/0065615 A1 | 4/2004 | Hooper |
| 2004/0068233 A1 | 4/2004 | DiMatteo |
| 2004/0082908 A1 | 4/2004 | Whitehurst |
| 2004/0111050 A1 | 6/2004 | Smedley |
| 2004/0204692 A1 | 10/2004 | Eliasen |
| 2004/0254536 A1 | 12/2004 | Conlon |
| 2004/0254537 A1 | 12/2004 | Conlon |
| 2004/0260229 A1 | 12/2004 | Meir |
| 2004/0260319 A1 | 12/2004 | Egle |
| 2004/0267288 A1 | 12/2004 | Byrum |
| 2004/0267291 A1 | 12/2004 | Byrum |
| 2004/0267292 A1 | 12/2004 | Byrum |
| 2004/0267293 A1 | 12/2004 | Byrum |
| 2004/0267377 A1 | 12/2004 | Egle |
| 2005/0010177 A1 | 1/2005 | Tsai |
| 2005/0049578 A1 | 3/2005 | Tu |
| 2005/0070875 A1 | 3/2005 | Kulessa |
| 2005/0070937 A1 | 3/2005 | Jambor |
| 2005/0085778 A1 | 4/2005 | Parks |
| 2005/0092093 A1 | 5/2005 | Kang |
| 2005/0131325 A1 | 6/2005 | Chen |
| 2005/0131352 A1 | 6/2005 | Conlon |
| 2005/0131383 A1 | 6/2005 | Chen |
| 2005/0148956 A1 | 7/2005 | Conlon |
| 2005/0149143 A1 | 7/2005 | Libbus |
| 2005/0209573 A1 | 9/2005 | Brugger |
| 2005/0240155 A1 | 10/2005 | Conlon |
| 2005/0240156 A1 | 10/2005 | Conlon |
| 2005/0267500 A1 | 12/2005 | Hassler |
| 2005/0277899 A1 | 12/2005 | Conlon |
| 2005/0283041 A1 | 12/2005 | Egle |
| 2005/0283118 A1 | 12/2005 | Uth |
| 2005/0283119 A1 | 12/2005 | Uth |
| 2006/0074439 A1 | 4/2006 | Garner |
| 2006/0095136 A1* | 5/2006 | McLuen .................... 623/23.47 |
| 2006/0122578 A1 | 6/2006 | Lord |
| 2006/0161186 A1 | 7/2006 | Hassler |
| 2006/0173423 A1 | 8/2006 | Conlon |
| 2006/0173424 A1 | 8/2006 | Conlon |
| 2006/0178647 A1* | 8/2006 | Stats .................... 604/288.01 |
| 2006/0178648 A1 | 8/2006 | Barron |
| 2006/0184141 A1 | 8/2006 | Smith |
| 2006/0189887 A1 | 8/2006 | Hassler |
| 2006/0189888 A1 | 8/2006 | Hassler |
| 2006/0190039 A1 | 8/2006 | Birk |
| 2006/0199997 A1 | 9/2006 | Hassler |
| 2006/0211912 A1 | 9/2006 | Dlugos |
| 2006/0211913 A1 | 9/2006 | Dlugos |
| 2006/0211914 A1 | 9/2006 | Hassler |
| 2006/0217668 A1 | 9/2006 | Schulze |
| 2006/0217673 A1 | 9/2006 | Schulze |
| 2006/0235445 A1 | 10/2006 | Birk |
| 2006/0235448 A1 | 10/2006 | Roslin |
| 2006/0247539 A1 | 11/2006 | Schugt |
| 2006/0266128 A1 | 11/2006 | Clark |

(56) References Cited

U.S. PATENT DOCUMENTS

| | | |
|---|---|---|
| 2006/0293625 A1 | 12/2006 | Hunt |
| 2006/0293626 A1 | 12/2006 | Byrum |
| 2006/0293627 A1 | 12/2006 | Byrum |
| 2006/0293628 A1 | 12/2006 | Hunt |
| 2007/0010790 A1 | 1/2007 | Byrum |
| 2007/0015954 A1 | 1/2007 | Dlugos |
| 2007/0015955 A1 | 1/2007 | Tsonton |
| 2007/0016231 A1 | 1/2007 | Jambor |
| 2007/0027356 A1 | 2/2007 | Ortiz |
| 2007/0038255 A1 | 2/2007 | Kieval |
| 2007/0049943 A1* | 3/2007 | Moskowitz et al. ............ 606/72 |
| 2007/0060959 A1 | 3/2007 | Salo |
| 2007/0073250 A1 | 3/2007 | Schneiter |
| 2007/0078391 A1 | 4/2007 | Wortley |
| 2007/0088336 A1 | 4/2007 | Dalton |
| 2007/0088391 A1 | 4/2007 | McAlexander |
| 2007/0129765 A1 | 6/2007 | Gilkerson |
| 2007/0135758 A1 | 6/2007 | Childers |
| 2007/0149947 A1 | 6/2007 | Byrum |
| 2007/0156013 A1 | 7/2007 | Birk |
| 2007/0158769 A1 | 7/2007 | You |
| 2007/0161958 A1 | 7/2007 | Glenn |
| 2007/0167672 A1 | 7/2007 | Dlugos |
| 2007/0173685 A1 | 7/2007 | Jambor |
| 2007/0185462 A1 | 8/2007 | Byrum |
| 2007/0191717 A1 | 8/2007 | Rosen |
| 2007/0205384 A1 | 9/2007 | Kurosawa |
| 2007/0208313 A1 | 9/2007 | Conlon |
| 2007/0213837 A1 | 9/2007 | Ferreri |
| 2007/0219510 A1 | 9/2007 | Zinn |
| 2007/0235083 A1 | 10/2007 | Dlugos |
| 2007/0250086 A1 | 10/2007 | Wiley |
| 2007/0255165 A1 | 11/2007 | Uesugi |
| 2007/0255234 A1 | 11/2007 | Haase |
| 2007/0265666 A1 | 11/2007 | Roberts |
| 2007/0282196 A1 | 12/2007 | Birk |
| 2007/0293829 A1 | 12/2007 | Conlon |
| 2008/0009680 A1 | 1/2008 | Hassler |
| 2008/0015406 A1 | 1/2008 | Dlugos |
| 2008/0039772 A1 | 2/2008 | Chantriaux |
| 2008/0058632 A1 | 3/2008 | Tai |
| 2008/0097496 A1 | 4/2008 | Chang |
| 2008/0114308 A1 | 5/2008 | Di Palma |
| 2008/0119798 A1 | 5/2008 | Chantriaux |
| 2008/0243093 A1 | 10/2008 | Kalpin |
| 2008/0249806 A1 | 10/2008 | Dlugos |
| 2008/0250340 A1 | 10/2008 | Dlugos |
| 2008/0250341 A1 | 10/2008 | Dlugos |
| 2008/0255403 A1 | 10/2008 | Voegele |
| 2008/0255414 A1 | 10/2008 | Voegele |
| 2008/0255425 A1 | 10/2008 | Voegele |
| 2008/0255459 A1 | 10/2008 | Voegele |
| 2008/0255537 A1 | 10/2008 | Voegele |
| 2008/0281412 A1 | 11/2008 | Smith |
| 2008/0287969 A1 | 11/2008 | Tsonton |
| 2008/0287974 A1 | 11/2008 | Widenhouse |
| 2008/0312553 A1 | 12/2008 | Timmons |
| 2008/0319435 A1 | 12/2008 | Rioux |
| 2009/0018608 A1 | 1/2009 | Schwartz |
| 2009/0048524 A1 | 2/2009 | Wildau |
| 2009/0054914 A1 | 2/2009 | Lechner |
| 2009/0062825 A1 | 3/2009 | Pool |
| 2009/0071258 A1 | 3/2009 | Kouda |
| 2009/0076466 A1 | 3/2009 | Quebbemann |
| 2009/0082757 A1 | 3/2009 | Rogers |
| 2009/0082793 A1 | 3/2009 | Birk |
| 2009/0093768 A1 | 4/2009 | Conlon |
| 2009/0099538 A1 | 4/2009 | Paganon |
| 2009/0105735 A1 | 4/2009 | Stam |
| 2009/0112308 A1 | 4/2009 | Kassem |
| 2009/0118572 A1 | 5/2009 | Lechner |
| 2009/0149874 A1 | 6/2009 | Ortiz |
| 2009/0157106 A1 | 6/2009 | Marcotte |
| 2009/0157107 A1 | 6/2009 | Kierath |
| 2009/0157113 A1 | 6/2009 | Marcotte |
| 2009/0171375 A1 | 7/2009 | Coe |
| 2009/0171378 A1 | 7/2009 | Coe |
| 2009/0171379 A1 | 7/2009 | Coe |
| 2009/0192404 A1 | 7/2009 | Ortiz |
| 2009/0192415 A1 | 7/2009 | Ortiz |
| 2009/0192533 A1 | 7/2009 | Dlugos |
| 2009/0192534 A1 | 7/2009 | Ortiz |
| 2009/0192541 A1 | 7/2009 | Ortiz |
| 2009/0198261 A1 | 8/2009 | Schweikert |
| 2009/0202387 A1 | 8/2009 | Dlugos |
| 2009/0204131 A1 | 8/2009 | Ortiz |
| 2009/0204132 A1 | 8/2009 | Ortiz |
| 2009/0209995 A1 | 8/2009 | Byrum |
| 2009/0216255 A1 | 8/2009 | Coe |
| 2009/0221974 A1 | 9/2009 | Paganon |
| 2009/0222031 A1 | 9/2009 | Axelsson |
| 2009/0222065 A1 | 9/2009 | Dlugos |
| 2009/0227862 A1 | 9/2009 | Smith |
| 2009/0228028 A1 | 9/2009 | Coe |
| 2009/0228072 A1 | 9/2009 | Coe |
| 2009/0248125 A1 | 10/2009 | Brostrom |
| 2009/0248126 A1 | 10/2009 | Nippoldt |
| 2009/0254052 A1 | 10/2009 | Birk |
| 2009/0259190 A1 | 10/2009 | Birk |
| 2009/0259191 A1 | 10/2009 | Birk |
| 2009/0259231 A1 | 10/2009 | Birk |
| 2009/0264901 A1* | 10/2009 | Franklin et al. ............... 606/139 |
| 2009/0270904 A1 | 10/2009 | Birk |
| 2009/0299216 A1 | 12/2009 | Chen |
| 2009/0299672 A1 | 12/2009 | Zhang |
| 2009/0306462 A1 | 12/2009 | Lechner |
| 2009/0308169 A1 | 12/2009 | Mothilal |
| 2010/0087843 A1 | 4/2010 | Bertolote |
| 2010/0100079 A1 | 4/2010 | Berkcan |
| 2010/0114149 A1 | 5/2010 | Albrecht |
| 2010/0130941 A1 | 5/2010 | Conlon |
| 2010/0152532 A1 | 6/2010 | Marcotte |
| 2010/0191271 A1 | 7/2010 | Lau |
| 2010/0211085 A1 | 8/2010 | Uth |
| 2010/0217198 A1 | 8/2010 | Franklin |
| 2010/0217199 A1 | 8/2010 | Uth |
| 2010/0217200 A1 | 8/2010 | Uth |
| 2010/0228080 A1 | 9/2010 | Tavori |
| 2010/0234808 A1 | 9/2010 | Uth |
| 2011/0054407 A1 | 3/2011 | Olroyd |
| 2011/0082426 A1 | 4/2011 | Conlon |

FOREIGN PATENT DOCUMENTS

| | | |
|---|---|---|
| EP | 1346753 | 9/2003 |
| EP | 1488824 A1 | 12/2004 |
| EP | 1543861 A1 | 6/2005 |
| EP | 1547643 | 6/2005 |
| EP | 1591140 A1 | 11/2005 |
| EP | 1736194 A1 | 12/2006 |
| EP | 1736195 | 12/2006 |
| EP | 1736196 | 12/2006 |
| EP | 1736197 | 12/2006 |
| EP | 1736198 | 12/2006 |
| EP | 1736199 | 12/2006 |
| EP | 1870126 | 12/2007 |
| EP | 1985263 | 10/2008 |
| EP | 2070494 A1 | 6/2009 |
| EP | 2095798 | 9/2009 |
| FR | 2823663 A1 | 10/2002 |
| JP | 2119877 | 5/1990 |
| JP | 8107934 | 4/1996 |
| WO | 9220519 A1 | 11/1992 |
| WO | 9422520 | 10/1994 |
| WO | 9640357 | 12/1996 |
| WO | 9701370 | 1/1997 |
| WO | 9920338 | 4/1999 |
| WO | 9926543 | 6/1999 |
| WO | 9934859 | 7/1999 |
| WO | 0015158 A1 | 3/2000 |
| WO | 0033901 | 6/2000 |
| WO | 0110359 A1 | 2/2001 |

(56) References Cited

FOREIGN PATENT DOCUMENTS

| | | | |
|---|---|---|---|
| WO | 0149245 | A2 | 7/2001 |
| WO | 0180926 | | 11/2001 |
| WO | 0195813 | A1 | 12/2001 |
| WO | 0210667 | A2 | 2/2002 |
| WO | 0274381 | | 9/2002 |
| WO | 03105732 | A1 | 12/2003 |
| WO | 2004016971 | | 3/2004 |
| WO | 2005037055 | A2 | 4/2005 |
| WO | 2005072627 | A1 | 8/2005 |
| WO | 2006021695 | | 3/2006 |
| WO | 2009007526 | | 1/2009 |
| WO | 2009129474 | A1 | 10/2009 |

OTHER PUBLICATIONS

Autumn K. et al.; 'Evidence of Van Der Waals Adhesion in Gecko Setae'; PNAS; vol. 99; No. 19; pp. 12252-12256; Sep. 17, 2012.

Geim Ak. et al.; 'Microfabricated Adhesive Mimicking Gecko Foot-Hair'; Nature Materials Abstract only; vol. 2; No. 7; 2003.

Yamagami, Takuji; 'Technical Developments; Use of Targeting Guide Wire in Left Subclavian Puncture During Percutaneous Implantation of Port-Catheter Systems Using the Catheter Tip Fixation Method' European Radiology; vol. 13; pp. 863-866; 2003.

Yurdumakan B., et al.; 'Synthetic Gecko Foot-Hairs from Multiwalled Carbon Nanotubes'; The Royal Society of Chemistry; p. 3799-3801; 2005.

* cited by examiner

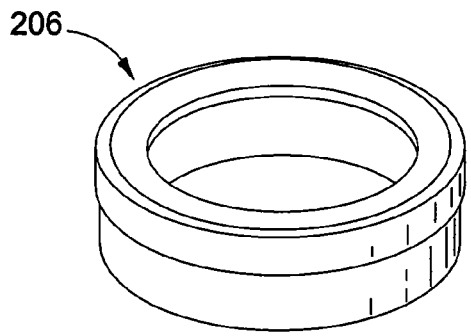
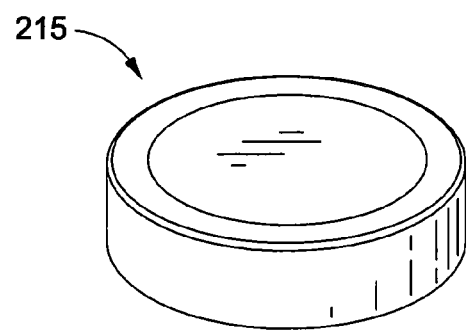
FIG. 6
FIG. 7
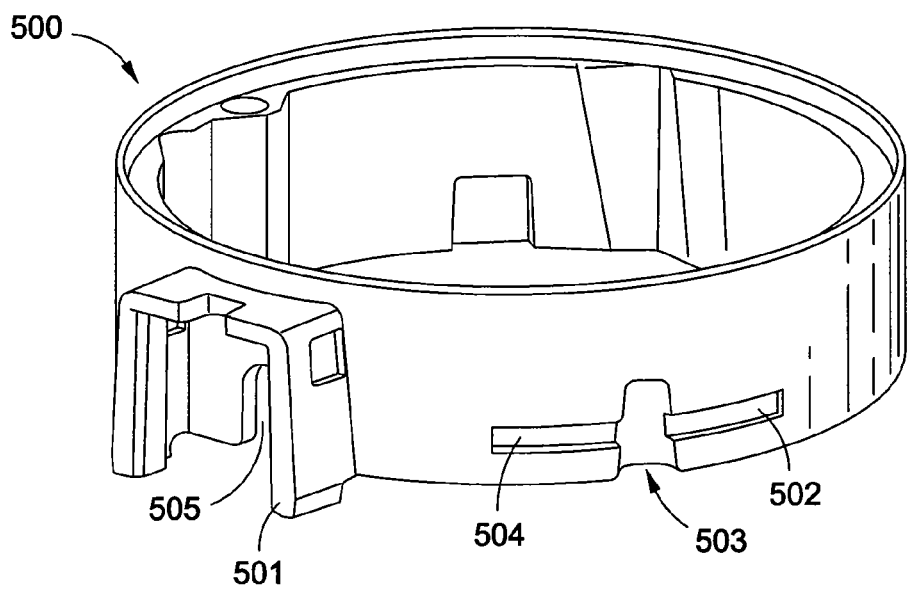
FIG. 8
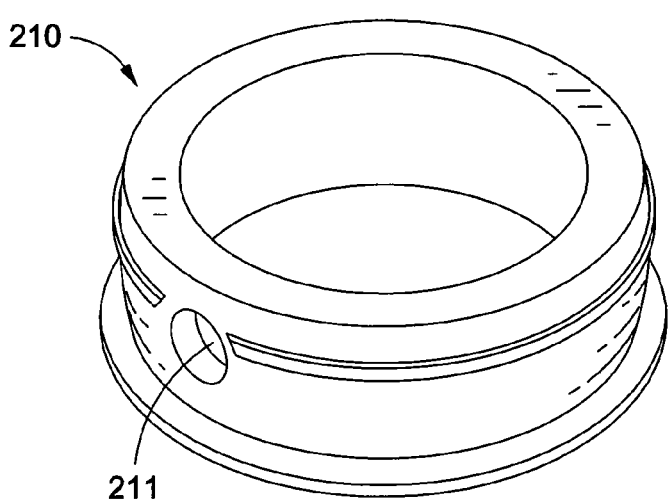
FIG. 9

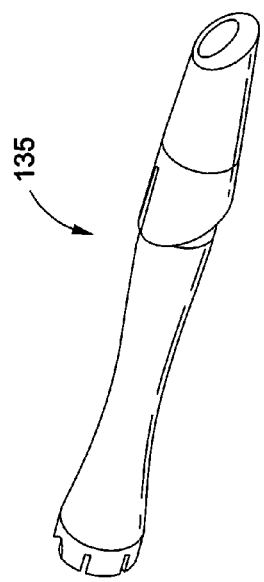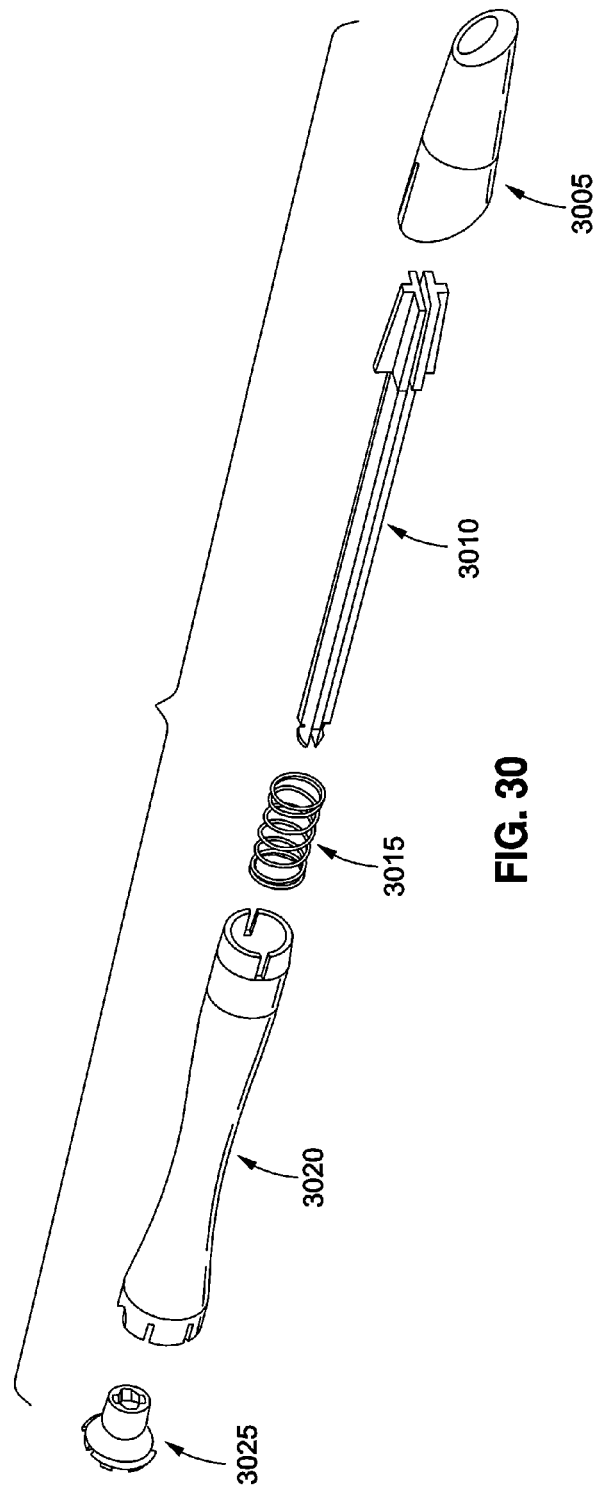

IMPLANTABLE ACCESS PORT SYSTEM

CROSS REFERENCE

This application is a continuation of U.S. patent application Ser. No. 12/857,447, filed Aug. 16, 2010, the entire contents of which is incorporated herein by reference.

BACKGROUND

1. Field

The present invention relates generally to implantable access ports and attachment mechanisms or systems for attaching the implantable access ports to a patient. More specifically, the present invention relates to implantable access ports with independent moving and locking gears for the anchors and related actuation devices. The implantable access ports may be connected to an inflatable portion of a gastric band and may be used to fill and remove fluid from the inflatable portion of the gastric band.

2. Description of the Related Art

Implantable medical devices for performing therapeutic functions for a patient are well known. Such devices include pace makers, vascular access ports, injection ports (such as those used with gastric banding devices) and gastric pacing devices. Such devices are attached to a human, typically subcutaneously, in an appropriate place in order to function properly. It is desirable that the procedure to implant such devices be quick, easy, efficient, and require as small of an incision as possible.

A suture (also known as stitches) is typically used by doctors to hold skin, internal organs, blood vessels and all other tissues of the human body together after they have been severed by injury, incision or surgery. Suturing is both time consuming and inconvenient. Surgical fasteners, such as staples, clips, clamps, bands, tacks, or other wound or incision closure devices, have been used in surgical procedures to eliminate the need for suturing. Surgical fasteners are commonly used in surgical procedures to allow a surgeon to fasten, secure, and/or repair bodily tissue. In these applications, the surgeon often uses a fastener implanting device loaded with one or more surgical fasteners to accomplish in a few seconds what would have taken many minutes to perform by suturing. This reduction in operating time reduces blood loss and trauma to the patient.

Typically, such surgical fasteners have been used mainly for the closure of incisions or wounds, or to fasten tissues together. A surgical fastener that can be used with a number of different types of implantable medical devices would be beneficial for surgeons. Currently, surgical systems that incorporate surgical fasteners often use extremely specialized devices that may be unnecessarily complicated and are unsuitable for adaptation to other applications.

As a result, the majority of implantable medical devices are secured with sutures. For example, when inserting a gastric band and an associated access port, the associated access port may be sutured into place with 3 to 5 sutures against the rectus muscle sheath. Such placement of the sutures is often challenging because the associated access port is placed below several inches of bodily tissue (e.g., fat), and suturing the associated access port often takes as long as placing the gastric band itself. An improved fastening device would allow easy, one-step attachment with security equivalent to the sutured medical device.

One conventional method for fastening an implantable access port to the patient includes an external pistol-like applying means. The external pistol may include a trigger having geared teeth, a gear which meshes with the geared teeth, and a spring. The external pistol attaches to the implantable access port and tightens a fastener into the tissue of the patient upon pressing of the trigger. After attachment, the external pistol is removed from the implantable access port.

Another conventional method for fastening an implantable access port includes fasteners extending from the housing of the implantable access port. In a self-attaching method, the implantable access port may be self attached upon the surgeon applying a distal force to the access port housing, causing the fasteners to penetrate the tissue, engaging the tissue to hold the access port in place. In an electronic method, the fasteners may be electronically switched between a deployed position and an un-deployed position using an actuator.

The present invention overcomes at least some of the drawbacks of these conventional medical devices and methods.

SUMMARY

Generally described herein are implantable access ports and related actuation devices. The apparatus, systems and methods described herein provide relatively easy attachment and locking capabilities of the implantable access ports to bodily tissue.

In one example embodiment, an implantable injection port for use with a gastric band for treating obesity and for attaching to a tissue of a patient is disclosed. The implantable injection port includes a base having an anchor opening, a gear coupled to the base and rotatable about a central axis, the gear having a plurality of gear teeth, an anchor coupled to the gear, and a top portion spaced apart from the base and having a plurality of top teeth that engage with the plurality of gear teeth. The top portion is rotatable causing rotation of the gear such that the rotation of the gear causes movement of the anchor through the anchor opening of the base and into the tissue of the patient.

BRIEF DESCRIPTION OF THE DRAWINGS

The features, objects, and advantages of the invention will become more apparent from the detailed description set forth below when taken in conjunction with the drawings, wherein:

FIG. 6 is a perspective view of the inner ring of FIG. 5 according to an embodiment of the present invention;

FIG. 7 is a perspective view of the septum of FIG. 5 according to an embodiment of the present invention;

FIG. 8 is a perspective view of the housing of FIG. 5 according to an embodiment of the present invention;

FIG. 9 is a perspective view of the reservoir of FIG. 5 according to an embodiment of the present invention;

FIGS. 29 and 30 are assembled and disassembled perspective views of the applier according to an embodiment of the present invention;

DETAILED DESCRIPTION

Apparatus, systems and methods that implement the embodiments of the various features of the present invention will now be described with reference to the drawings. The drawings and the associated descriptions are provided to illustrate some embodiments of the present invention and not to limit the scope of the present invention. Throughout the drawings, reference numbers are re-used to indicate correspondence between referenced elements.

A system is disclosed having a port (e.g., an implantable access port or an implantable injection port) that is securely fastened to bodily tissue of a human or a patient. The port is used to fill and remove fluid from an inflatable portion of a band (e.g., a gastric band) via a catheter attached between the port and the inflatable portion of the band. One or more anchors (e.g., four anchors) of the port may be subcutaneously and securely attached to the bodily tissue of the human by rotating one or more mating components (e.g., an applier, an axle, a cap, a gear, etc.). The one or more mating components provide a continually secure attachment of the one or more anchors to the bodily tissue of the patient after surgery.

Figure 1:
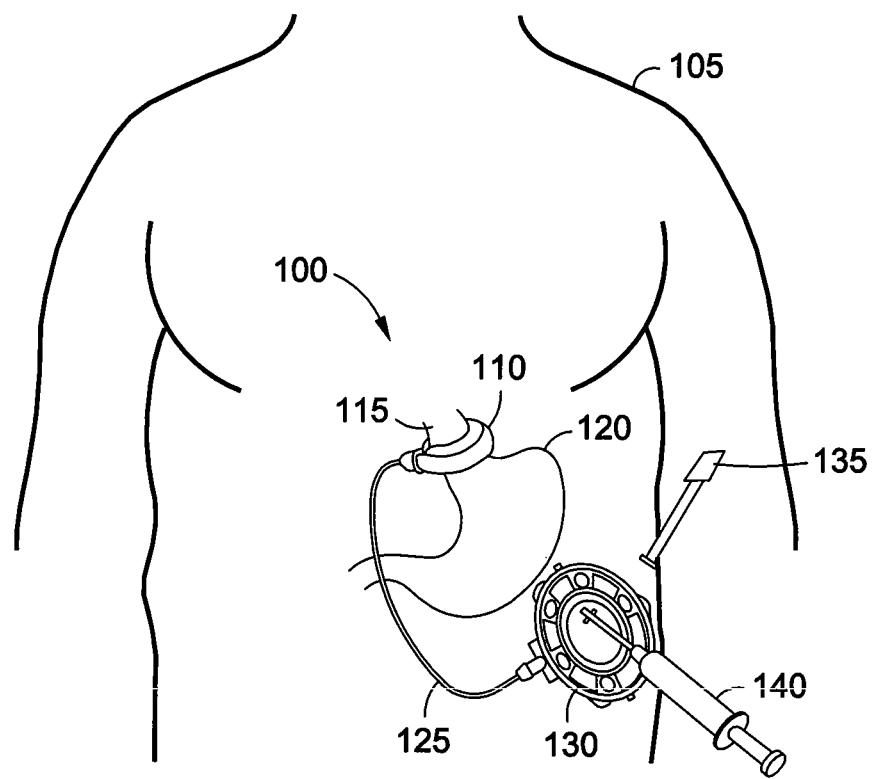
FIG. 1 is a simplified partial front view of a human body with a food intake restriction system having a band, a port and an applier tool according to an embodiment of the present invention.

FIG. 1 is a simplified partial front view of a human body 105 with a food intake restriction system 100 having a band 110, a port 130 and an applier 135 according to an embodiment of the present invention. The food intake restriction system 100 is used to treat obesity and to attach to a tissue of a patient. The band 110 may be a gastric band, such as the Lap-Band®, and may be adjustable, implantable, inflatable and positioned around or near the upper portion of a stomach 120 of a human 105. Generally, the band 110 is placed about the fundus, or esophageal junction, of a patient's upper stomach forming a stoma that restricts the food's passage into a lower portion of the stomach. The band 110 may include an inflatable portion (e.g., a cavity) made of silicone rubber, or another type of biocompatible material, that inflates or expands inward to constrict the stoma (stomach inlet) when filled with a fluid (e.g., saline) from a catheter 125. Alternatively, a mechanical device or a combination hydraulic/mechanical device may be coupled to the band 110 to constrict the stoma. When the stoma is of an appropriate size that is restricted by the band 110, food held in the upper portion of the stomach may provide a feeling of satiety or fullness that discourages overeating.

The port 130 may be implanted in a body region accessible for needle injections from a syringe 140 and/or for receiving telemetry communication signals. The port 130 is a medical device that may be referred to as an access port, an injection port, an implantable access device or a housing. The port 130 fluidly communicates with the inflatable portion of the band 110 via the catheter 125.

A medical professional (e.g., doctor, health care provider, nurse, surgeon, technician, etc.) may position and temporarily or permanently implant the port 130 inside the body of the human 105 in order to perform adjustments of the food intake restriction or stoma created by the band 110. The medical professional, for example, may implant the port 130 in the lateral, subcostal region of the human's abdomen under the skin and layers of fatty tissue, or on or near the sternum of the human 105. Also, any other suitable attachment areas or port sites may be used.

The applier 135 may be used to secure the port 130 to the human 105, as rotation of an applier handle rotates a portion of the port 130 and secures anchors of the port 130 into bodily tissue of the human 105. In particular, the anchors may be moved from an undeployed position to a deployed position. The applier 135 may be a tool such as a delivery tool.

Figure 2:
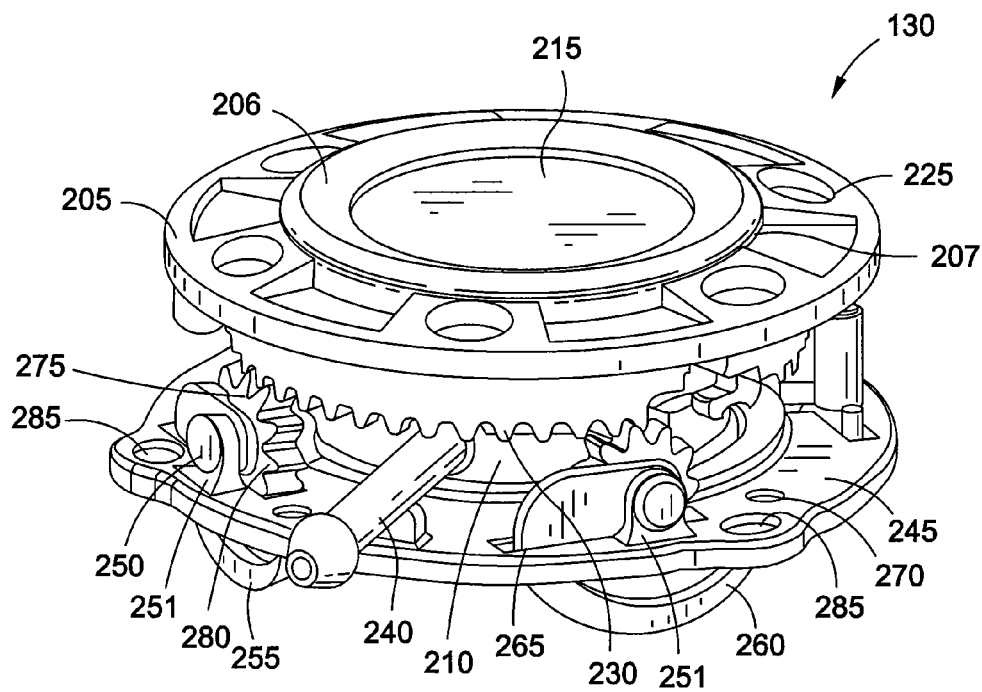
FIG. 2 is a perspective view of the port according to an embodiment of the present invention.
Figure 3:
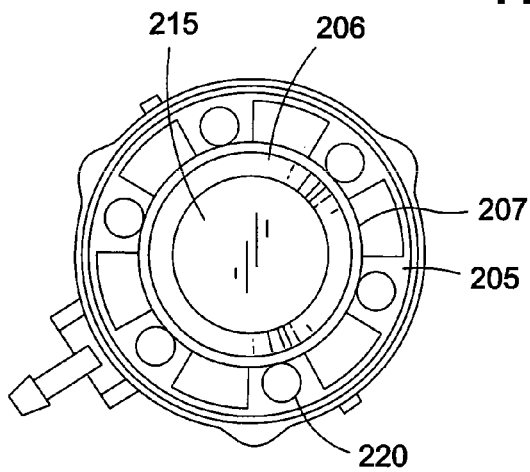
FIG. 3 is a top view of the port of FIG. 2, illustrating a circular fitting that connects to or meshes with the applier, according to an embodiment of the present invention.
Figure 4:
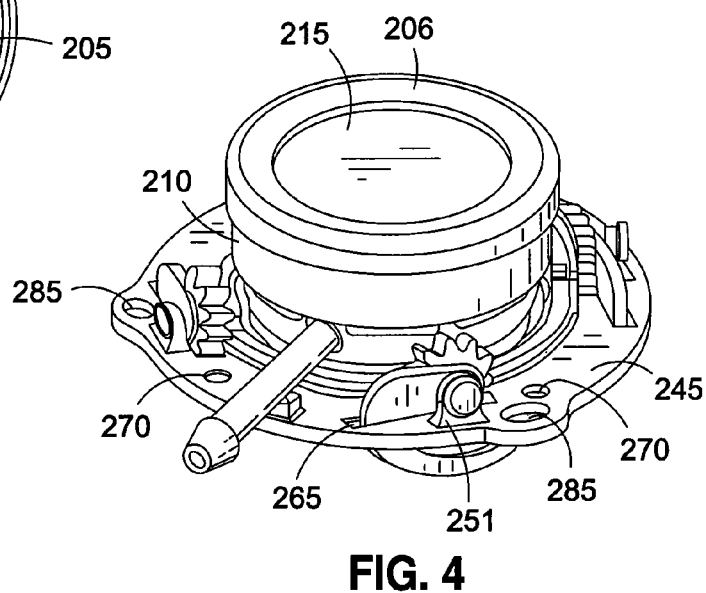
FIG. 4 is a perspective view of the port of FIG. 2 with a top portion removed to show the reservoir according to an embodiment of the present invention.
Figure 5:
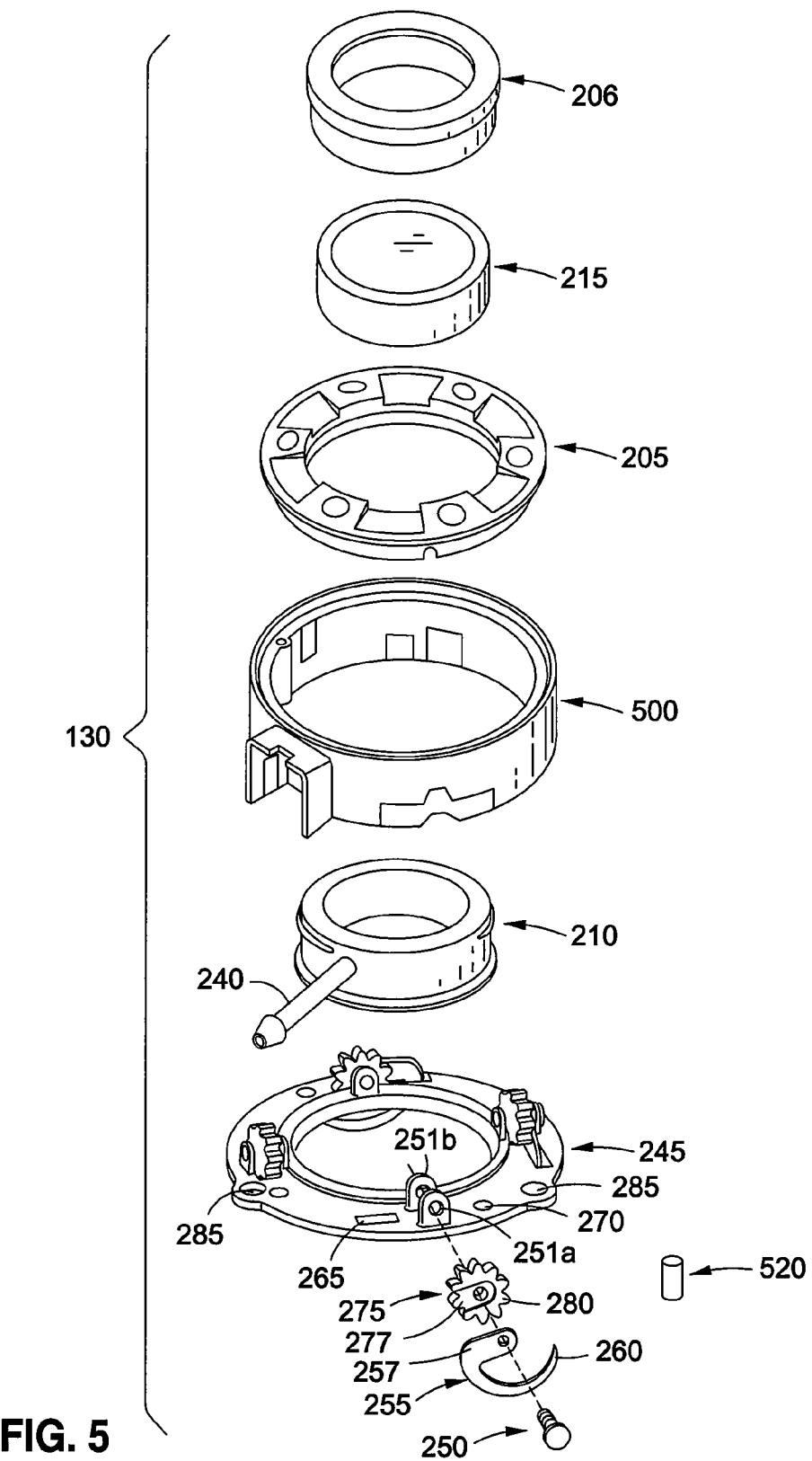
FIG. 5 is a disassembled perspective view showing the different parts of the port of FIG. 2 according to an embodiment of the present invention.

FIG. 2 is a perspective view of the port 130 according to an embodiment of the present invention. FIG. 3 is a top view of the port 130 of FIG. 2, illustrating a circular fitting 207 that connects to or meshes with the applier 135, according to an embodiment of the present invention. FIG. 4 is a perspective view of the port 130 of FIG. 2 with a top portion 205 removed to show the reservoir 210 according to an embodiment of the present invention. FIG. 5 is a disassembled perspective view showing the different parts of the port 130 of FIG. 2 according to an embodiment of the present invention.

Referring to FIGS. 1-5, the port 130 is configured to receive fluid from the syringe 140 for movement into the inflatable portion of the band 110. The port 130 includes the top portion 205 and the reservoir 210. The reservoir 210 contains an interior space for holding the fluid. The reservoir 210 may be an internal titanium port reservoir or a port without the top portion 205. As shown in FIG. 4, the reservoir 210 is formed in the shape of a cylinder.

The top portion 205 may be a drive cap, a port cap, a rotating cap, a top cap or a top outer ring. The top portion 205 may be attached to or be integrally formed with an inner ring 206. The inner ring 206 may also be referred to as a flange. Alternatively, the top portion 205 may include the inner ring 206.

The top portion 205 may have a center opening 207. The center opening 207 allows the inner ring 206 to fit therein. In addition, a septum 215 (e.g., a needle penetrable septum) may be located or positioned within the inner ring 206 and/or the center opening 207 of the top portion 205. The inner ring 206 and/or the septum 215 may be attached to the reservoir 210. The top portion 205 can rotate without rotating the inner ring 206 and/or the septum 215. That is, the inner ring 206 and/or the septum 215 may be permanently attached or fixedly attached to the reservoir 210. In one embodiment, the top portion 205 is moveably or rotatably attached to the inner ring 206.

As an example, the syringe 140 may be used to pierce the septum 215, thus allowing the fluid in the syringe 140 to pass into the reservoir 210 and then ultimately through the catheter 125 and into the inflatable portion of the band 110. Also, the syringe 140 may be used to remove fluid from the reservoir 210, which causes the fluid in the inflatable portion of the band 110 to be removed therefrom. The septum 215 may be made of any suitable needle penetrable material, for example, a self sealing needle penetrable material.

The top portion 205 may also have one or more fittings 207 (e.g., cavities, holes or notches) located on a top surface of the top portion 205 to allow the applier 135 to attach to or mate with the top portion 205. The fittings 207 may be referred to as snap fittings because the applier 135 can snap into and out of the fittings 207. Located in or near the fittings 207, can be a lock indicator 225, illustrating when the port 130 is securely attached to the bodily tissue of the human 105. For example, the lock indicator 225 can be a color-coded indicator on a bottom surface of the fittings 207 where a green color indicates a locked position and a red color indicates an unlocked position. The applier 135 can mate with the top portion 205 to rotate the top portion 205. In one embodiment, the top portion 205 rotates in a circular direction guided by the applier 135.

The top portion 205 may also have teeth 230 protruding from a bottom surface of the top portion 205. In an example embodiment, the teeth 230 are positioned along an axis that is substantially perpendicular to a plane defined by the top portion 205. The teeth 230 include ridges, alternating cut-outs and protrusions, bumpy or uneven surfaces, a flat surface with friction and/or any other surface(s) with sufficient friction to interact with and move components (e.g., the gear 275 and the anchor 255) of the port 130. The teeth 230 may be positioned along an outer edge of the entire top portion 205 forming a circle.

The port 130 has a base 245, one or more axles 250, one or more axle holders 251, one or more gears 275 and one or more anchors 255. The base 245 may also be referred to as a port base, a bottom base, a bottom cap, a bottom ring or a bottom portion. The base 245 may lie along a plane that is substantially parallel to the plane defined by the top portion 205. The reservoir 210 is fixedly attached to the base 245 and does not move with the rotation of the top portion 205. The base 245 includes one or more anchor openings 265 and one or more tip openings 270. As an example, the one or more anchor openings 265 may be formed in the shape of a rectangle and the one or more tip openings 270 may be formed in the shape of a circle.

The axle holder 251 is attached to or integrated with the base 245. The axle holder 251 may include two pylons 251a and 251b each having a hole for the axle 250 to pass therethrough (see FIG. 5). The two pylons 251a and 251b are positioned adjacent to and on opposite sides of the anchor opening 265. The anchor 255 and the gear 275 also have openings that allow for the axle 250 to pass therethrough. As shown in FIG. 5, the gear 275 may have a side groove 277 for holding the anchor 255 in place and allowing for simultaneous rotation. In an assembled state, a base portion 257 of the anchor 255 tightly fits into the side groove 277 of the gear 275 and the combined anchor 255 and gear 275 fit between the two pylons 251a and 251b. The axle 250 passes through the holes of the pylon 251a, the anchor 255, the gear 275, and the pylon 251b and is positioned therein. The movement of the gear 275 causes a similar circular or rotational movement of the anchor 255.

The axle 250 may rotate circularly when force is applied thereon. The axle 250 may also be referred to as a center pin. The gear 275, attached to the axle 250, may rotate in unison with the axle 250.

The gear 275 may also be referred to as a pinion gear. The gear includes teeth 280 which mate with the teeth 230 of the top portion 205 to rotate the anchor 255. The teeth 280 may include ridges, bumpy surfaces, flat surfaces with friction, and any other surface with sufficient friction to interact with and to move components of the port 130.

To deploy the anchor 255, the top portion 205 is rotated in a clockwise direction and the teeth 230 are engaged with the teeth 280 to rotate the gear 275 and the anchor 255 in a counter-clockwise direction causing the anchor 255 to move through the anchor opening 265 and into the tissue of a patient. An anchor tip 260 may also move into the tip opening 270 when the anchor 255 is fully deployed.

The anchor 255 secures the port 130 to the human 105, by the anchor tip 260 penetrating the human's skin or muscle (e.g., abdominal muscle fascia). The anchor tip 260 may also be referred to as a hook or pointed end. The anchor tip 260 is structured to penetrate and enter the bodily tissue as the anchor 255 rotates into the deployed position. In some embodiments, the anchor tip 260 includes one or more flat faces. For example, the anchor tip 260 may have a single facet, or may have two or more facets. The anchor 255 may also be referred to as an attachment mechanism, a hook, a needle anchor, a needle device, or a cork screw. Also, the anchor 255 may be formed in the shape of a hook, a needle or a cork screw (e.g., a series of spirals with a sharp point at the end of the series of spirals (see FIGS. 24 and 25)). In one embodiment, each anchor 255 may be made of a wire, for example, a bent stainless steel wire having a round cross section and a multi-faceted sharp distal tip. The port 130 may include two, three, four, five or more anchors 255 and related components that are attached and positioned an equi-distance around the base 245.

Figure 20:
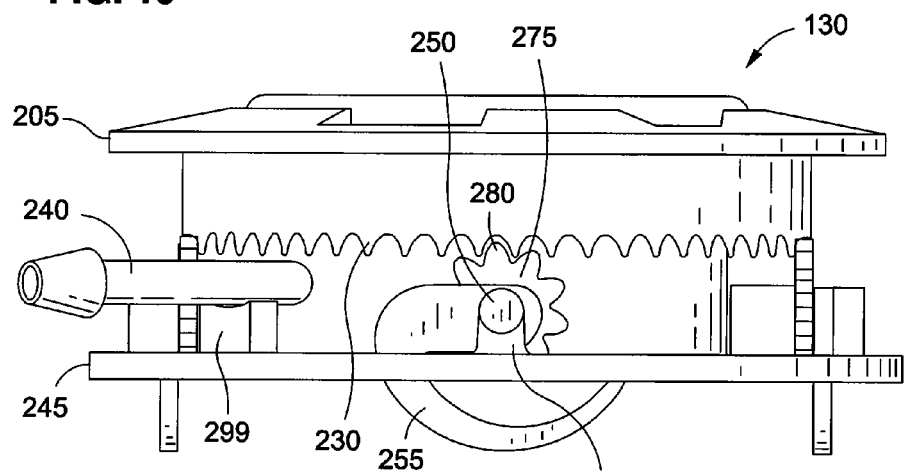
FIG. 20 is a side view of the top teeth engaged with the bottom teeth according to an embodiment of the present invention.
Figure 21:
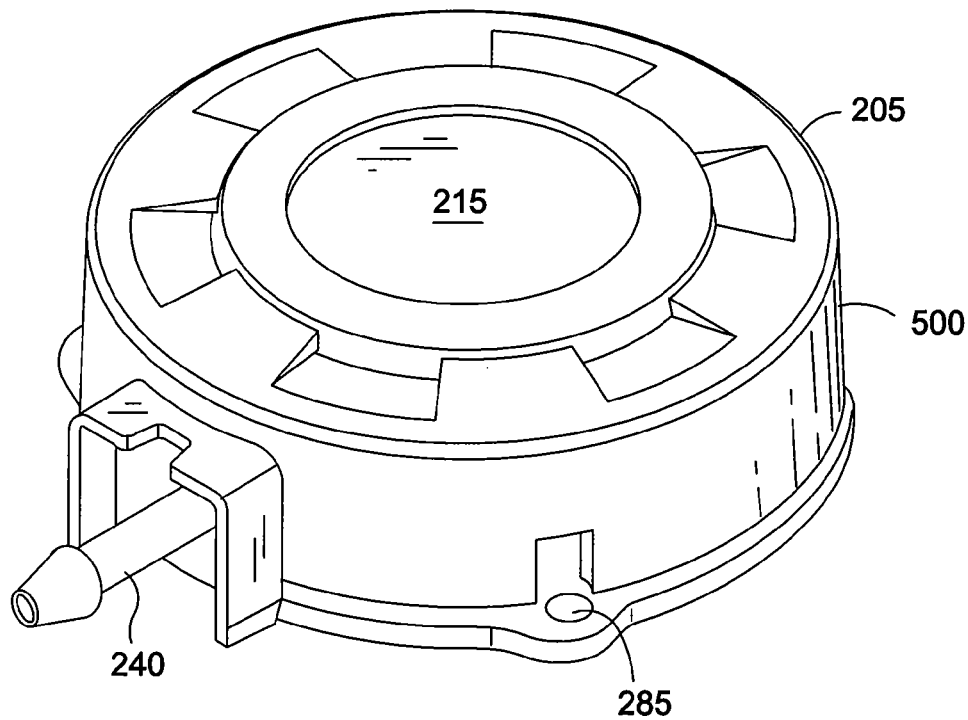
FIGS. 21 and 22 are perspective top and side views of the housing with the top portion, the base and the anchors according to an embodiment of the present invention.

In one embodiment, a plurality of anchors 255 are simultaneously deployed or moved from an un-deployed position (FIG. 20) to a deployed position (FIG. 21). Each anchor 255 is rotated from an un-deployed position where the anchor 255 is above the base 245 to a deployed position where the anchor 255 travels through the anchor opening 265 and the base portion 257 of the needle 255 is in direct contact with the base 245. When in the deployed position, the anchors 255 fix the port 130 to the bodily tissue. In the case where the port 130 is used in conjunction with a gastric band, the port 130 may be secured, by means of the anchors 255, to the rectus muscle fascia. The anchor 255 may protrude through the anchor opening 265 in the base 245, and may also protrude through the tip opening 270 in the base 245 as the anchor 255 is rotated around the axle 250. The tip opening 270 provides a safe storage position for the anchor tip 260 so the anchor tip 260 does not get dulled or damaged. The positioning of the anchor tip 260 can be adjusted by having an anchor 255 with different base portion 257 thicknesses, as the anchor 255 can rotate until the base portion 257 of the anchor 255 contacts the base 245.

The base 245 may also have one or more suture holes 285 for suturing the port 130 to the human 105, in the event that the use of the applier 135 to attach the port 130 is not desired or allowable. A drawback of suturing is the additional time and effort required by the medical professional to secure the port 130 during surgery.

In some embodiments, the anchors 255 are simultaneously removable or reversible, allowing the anchors 255 to be detached from the bodily tissue. For example, the top portion 205 can be rotated in a counter-clockwise direction to remove the anchors 255 from the tissue. Specifically, to un-deploy the anchors 255, the cap 205 is rotated in a counter-clockwise direction and the teeth 230 are engaged with the teeth 280 to rotate the gear 275 and the anchor 255 in a clockwise direction causing the anchors 255 to move through the anchor opening 265 and out of the tissue. The anchor tip 260 may also move into the anchor opening 265.

In one embodiment, a plurality of anchors 255 includes four anchors that are evenly spaced apart around the base 245. Each anchor 255 may be referred to as being independent, which includes being a separate component or having separate operation from another anchor 255. Each anchor 255 includes a curved distal portion or anchor tip 260 which engages the bodily tissue and a pivotal proximal portion or body portion 257, which is rotatably connected to the base 245 of the port 130. In some embodiments, the pivotal proximal portion is substantially perpendicular with the curved distal portion, or more specifically, substantially perpendicular with a plane in which the curved distal portion rotates when the anchors are moved into the deployed position. In some embodiments, each anchor 255 may include a generally spiral distal portion and a straight proximal portion substantially perpendicular with the spiral distal portion.

The port 130 may further include a removable safety cap (not shown) to protect the medical professional's hands and fingers from accidental anchor sticks. The safety cap may mount to the bottom of the port 130 by a press-on fit. The color of the safety cap may be easily distinguishable from the color of the port 130.

The base 245 may be moveably attached to the top portion 205 by the reservoir 210. A stem 240 is attached to the reservoir 210 for injecting the fluid from the port 130 to the band 110. The stem 240 may include a strain relief element which locks into the housing 500 and protects the catheter 125 from folding, kinking, rotating, or torquing when the catheter 125 is connected to the reservoir 210. Further strain relief may be provided by a flexible sleeve made of a puncture resistance material. The flexible sleeve and the strain relief element provide protection against accidental needle punctures to the catheter 125.

Referring to FIG. 5, the disassembled perspective view showing the different parts of the port 130 of FIG. 2 discloses the inner ring 206, the septum 215, the top portion 205, the housing 500, the reservoir 210 and the stem 240, the base 245 and the related components and a radiopaque marker 520. The inner ring 206 may also include a titanium palpation ring.

The housing 500 may also be referred to as a port housing. The housing 500 surrounds the port 130 and covers the components therein.

The radiopaque marker 520 is a type of locator element on the port 130 that is clearly visible under an x-ray. The radiopaque marker 520 may be secured in the housing 500 so as not to hide the radiopaque marker 520. The radiopaque markers 520 can be used to facilitate identification of the type of gastric band or other useful information to be identified by the x-ray image of the port 130, for example, by using varied configurations, sizes or shapes of the radiopaque marker 520.

FIG. 6 is a perspective view of the inner ring 206 of FIG. 5 according to an embodiment of the present invention. FIG. 7 is a perspective view of the septum 215 of FIG. 5 according to an embodiment of the present invention.

FIG. 8 is a perspective view of the housing 500 of FIG. 5 according to an embodiment of the present invention. A coupler 501 is attached to an exterior surface of the housing 500 for attachment to the applier 135. The stem 240 extends through an opening 505 in the housing 500. A plurality of slits or openings 502, 503 and 504 in the housing 500 are used for attachment to the applier 135. In one embodiment, the center slit or opening 503 is a suture cutout that are aligned with the suture holes 285 on the base 245. FIG. 9 is a perspective view of the reservoir 210 of FIG. 5 according to an embodiment of the present invention. The reservoir 210 has an opening 2100 for the stem 240 for connection to the reservoir 210.

Figure 10:
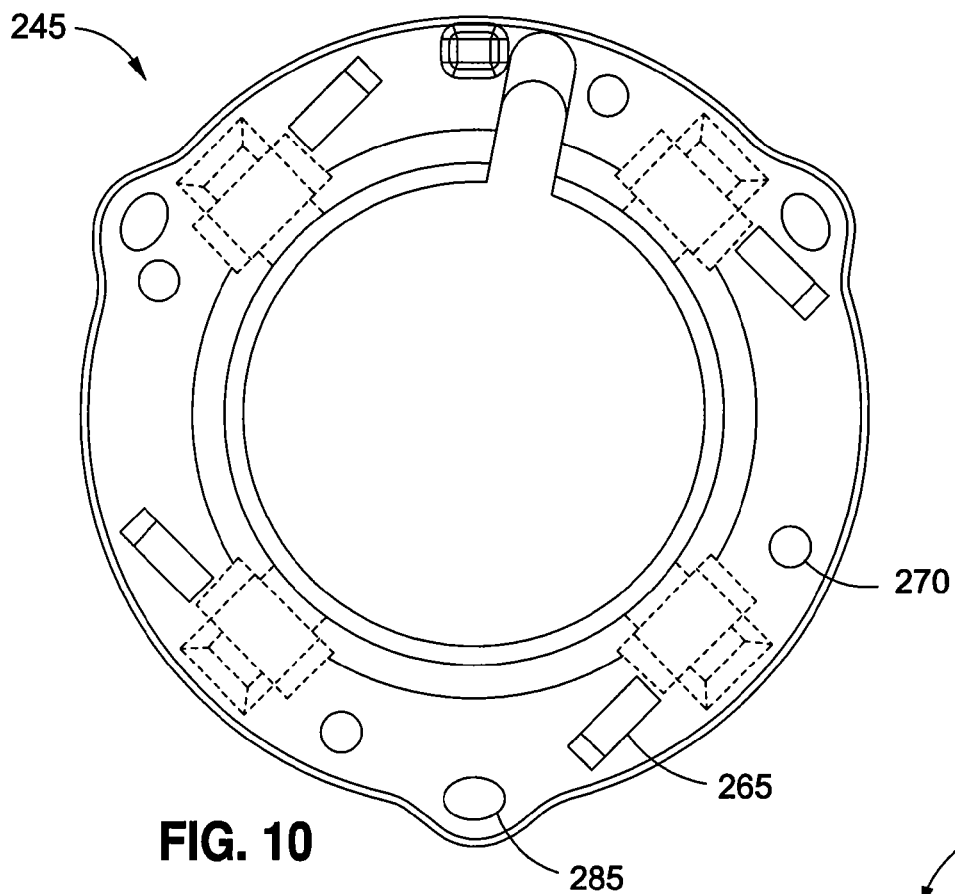
FIG. 10 is a bottom view of the base showing the anchor opening, the tip opening and the one or more suture holes according to an embodiment of the present invention.

FIG. 10 is a bottom view of the base 245 showing the anchor opening 265, the tip opening 270, and the one or more suture holes 285 according to an embodiment of the present invention.

Figure 11:
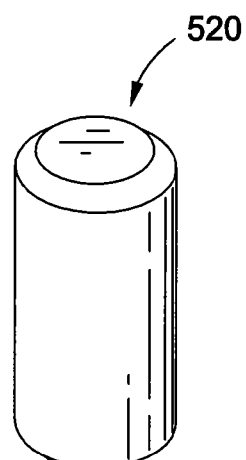
FIG. 11 is a perspective view of the radiopaque marker according to an embodiment of the present invention.

FIG. 11 is a perspective view of the radiopaque marker 520 according to an embodiment of the present invention. As an example, the radiopaque marker 520 is formed in the shape of a cylinder.

Figure 12:
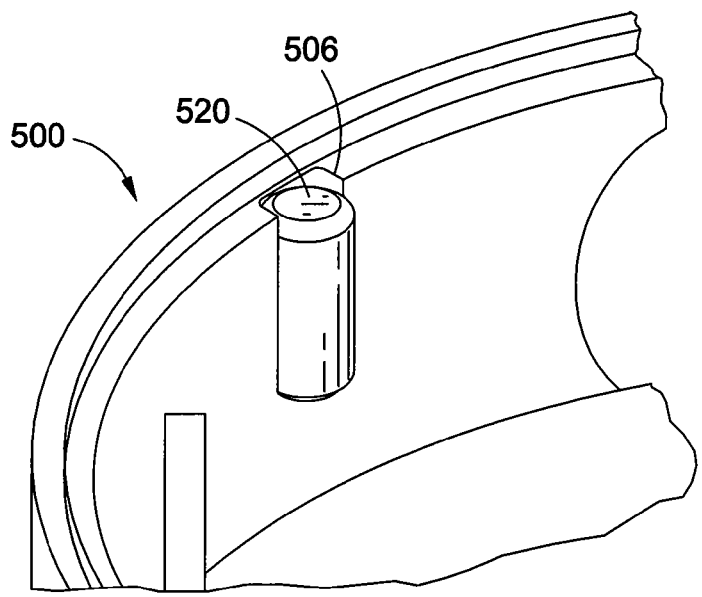
FIG. 12 is a partial perspective view of the housing showing the radiopaque marker embedded into an inner cutout of the housing according to an embodiment of the present invention.

FIG. 12 is a partial perspective view of the housing 500 showing the radiopaque marker 520 embedded into an inner cutout 506 of the housing 500 according to an embodiment of the present invention. As shown, the radiopaque marker 520 fits snugly into the inner cutout 506.

Figure 13:
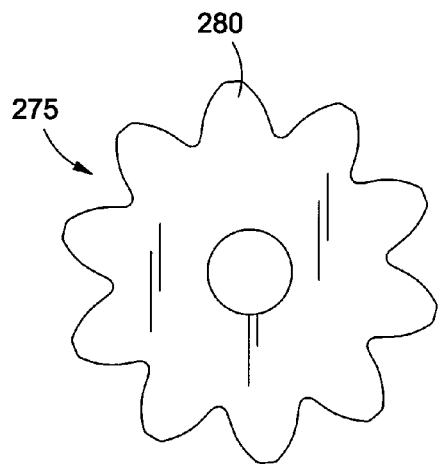
FIG. 13 is a side view of the gear with the teeth according to an embodiment of the present invention.

FIG. 13 is a side view of the gear 275 with the gear teeth 280 according to an embodiment of the present invention.

Figure 14:
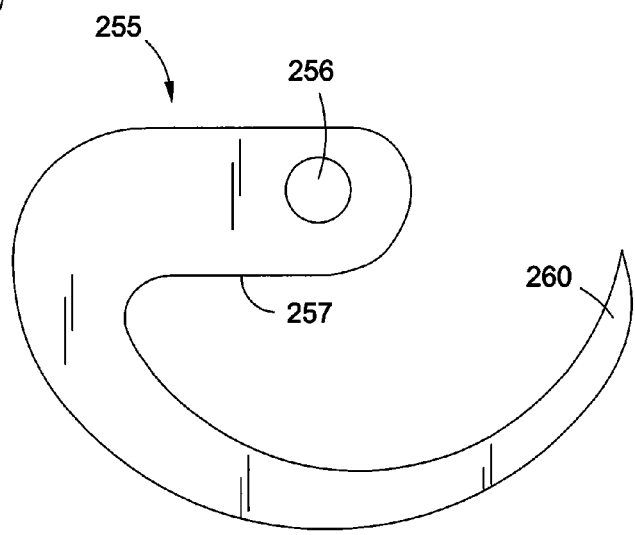
FIG. 14 is a side view of the anchor having a first hole, the base portion and the anchor tip according to an embodiment of the present invention.

FIG. 14 is a side view of the anchor 255 having a first hole 256, the base portion 257 and the anchor tip 260 according to an embodiment of the present invention. The axle 250 (not shown) is positioned through the first hole 256.

Figure 15:
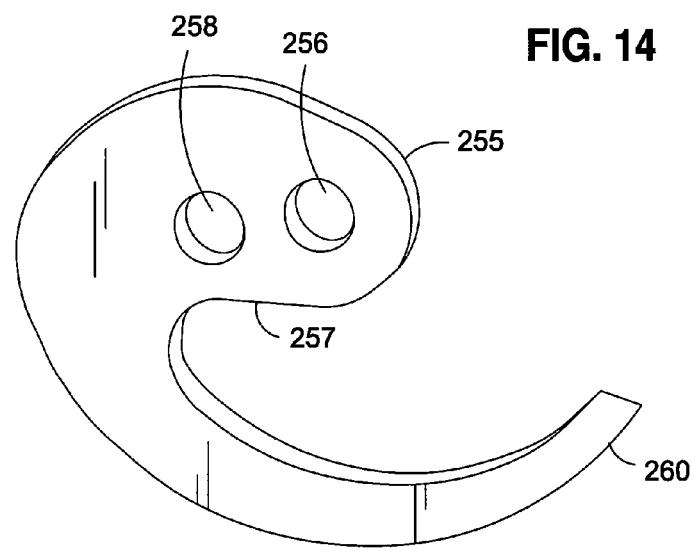
FIG. 15 is a side view of the anchor having a first hole and a second hole according to an embodiment of the present invention.

FIG. 15 is a side view of the anchor 255 having a first hole 256 and a second hole 258 according to an embodiment of the present invention. The axle 250 (not shown) is positioned through the first hole 256. The second hole 258 is formed in the shape of a circle.

Figure 16:
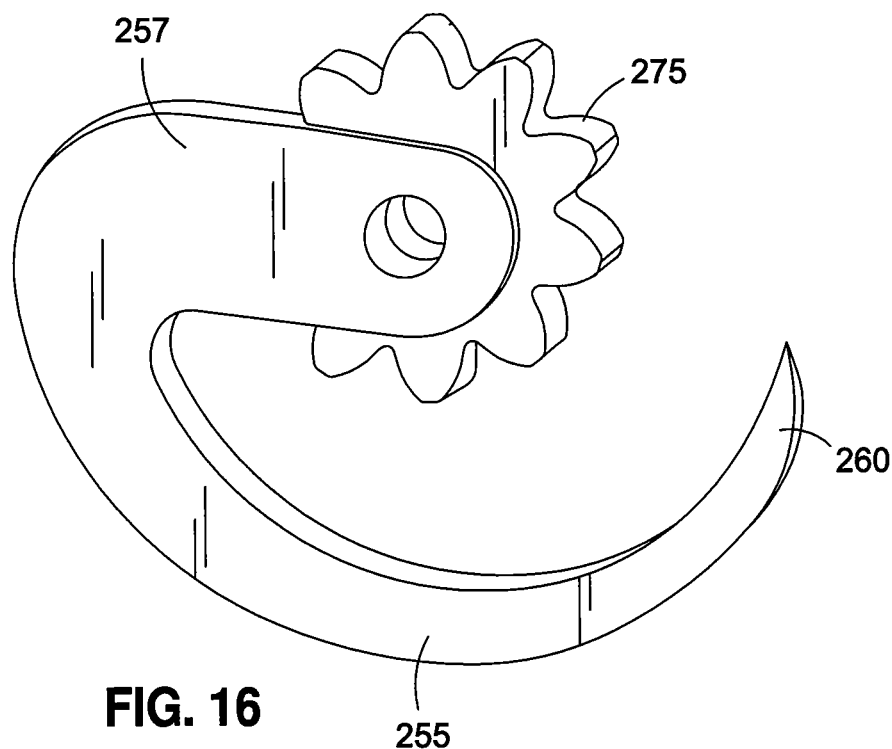
FIG. 16 is a side view of the anchor connected to the gear according to an embodiment of the present invention.

FIG. 16 is a side view of the anchor 255 connected to the gear 275 according to an embodiment of the present invention. The gear 275 is secured to a middle portion of the anchor 255. The gear 275 and the anchor 255 rotate together.

Figure 17:
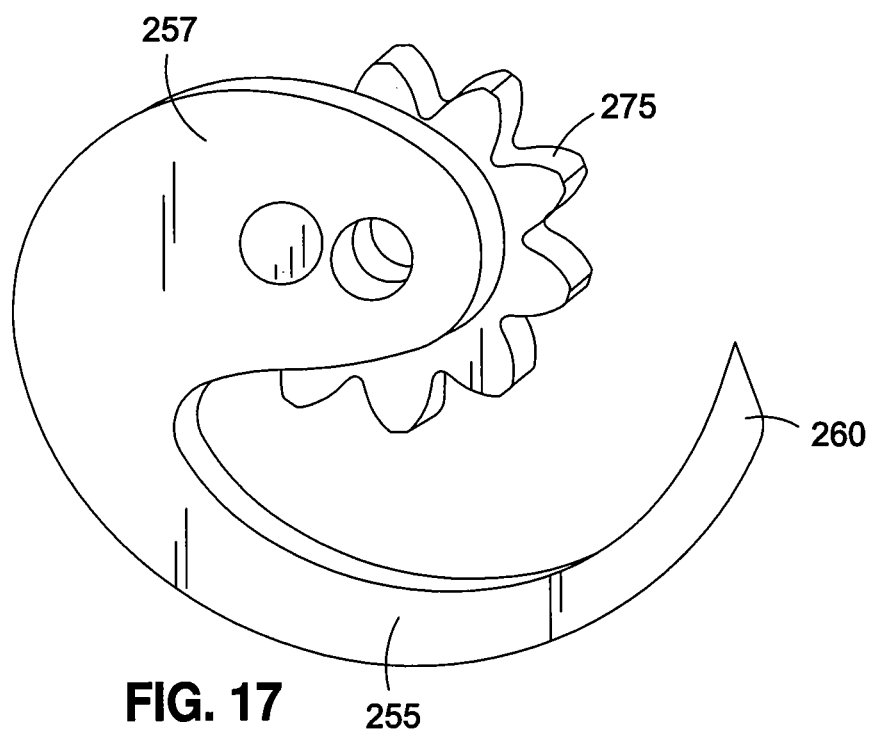
FIG. 17 is a side view of the anchor connected to the gear according to an embodiment of the present invention.

FIG. 17 is a side view of the anchor 255 connected to the gear 275 according to an embodiment of the present invention. The gear 275 is secured to a side portion of the anchor 255. The gear 275 and the anchor 255 rotate together.

Figure 18:
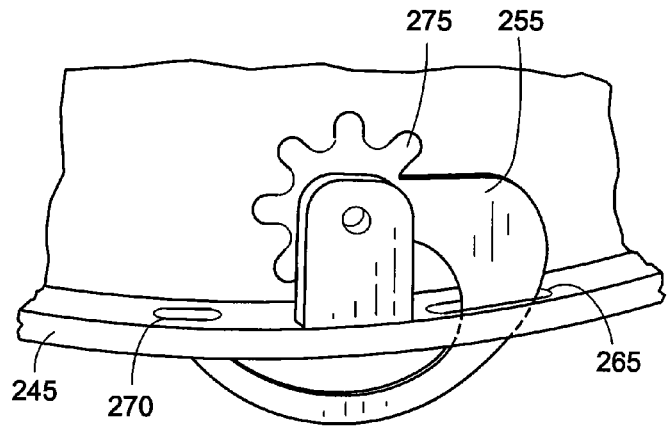
FIG. 18 is an exploded side view of the gear and the anchor in a deployed position according to an embodiment of the present invention.

FIG. 18 is an exploded side view of the gear 275 and the anchor 255 in a deployed position where the anchor 255 is positioned through the anchor opening 265 in the base 245 and the anchor tip 260 is positioned within the tip opening 270 in the base 245 according to an embodiment of the present invention.

Figure 19:
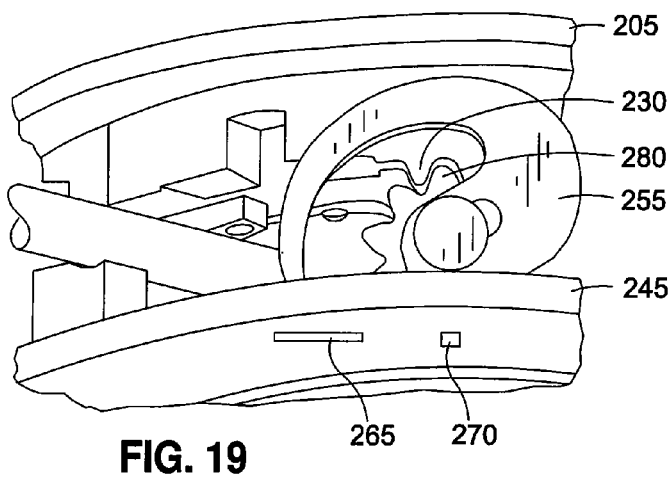
FIG. 19 is an exploded side view of the gear and the anchor in an un-deployed position where the anchor is positioned between the top portion and the base according to an embodiment of the present invention.

FIG. 19 is an exploded side view of the gear 275 and the anchor 255 in an un-deployed position where the anchor 255 is positioned between the top portion 205 and the base 245 according to an embodiment of the present invention. The top teeth 230 are in movable engagement with the bottom teeth 280. As the top portion 205 is rotated, the top teeth 230 move, which in turn moves the bottom teeth 280, which rotate the anchor 255.

FIG. 20 is a side view of the top teeth 230 engaged with the bottom teeth 280 according to an embodiment of the present invention. When the anchor 255 is in the fully deployed position, the stem 240 is locked in place by a locking member 299, which is attached to the base 245. The locking member 299 has a concave top surface that mates with a convex top surface of the locking member 299.

Figure 22:
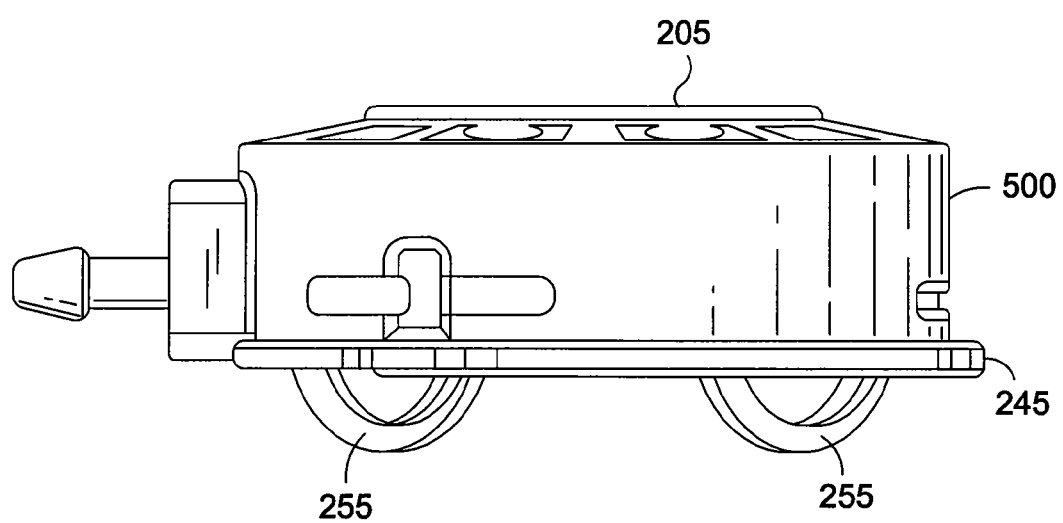

FIGS. 21 and 22 are perspective top and side views of the housing 500 with the top portion 205 and the base 245 according to an embodiment of the present invention. As shown, the anchors 255 protrude from the base 245 and form a curve when the anchors 255 are in a deployed position.

Figure 23:
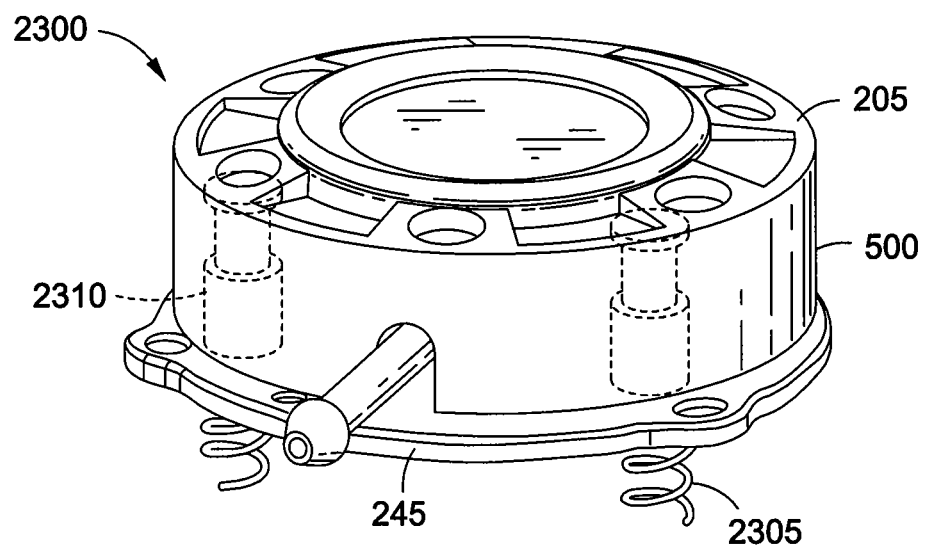
FIGS. 23 and 24 are perspective top and bottom views of a port having cork screw anchors according to an embodiment of the invention.
Figure 24:
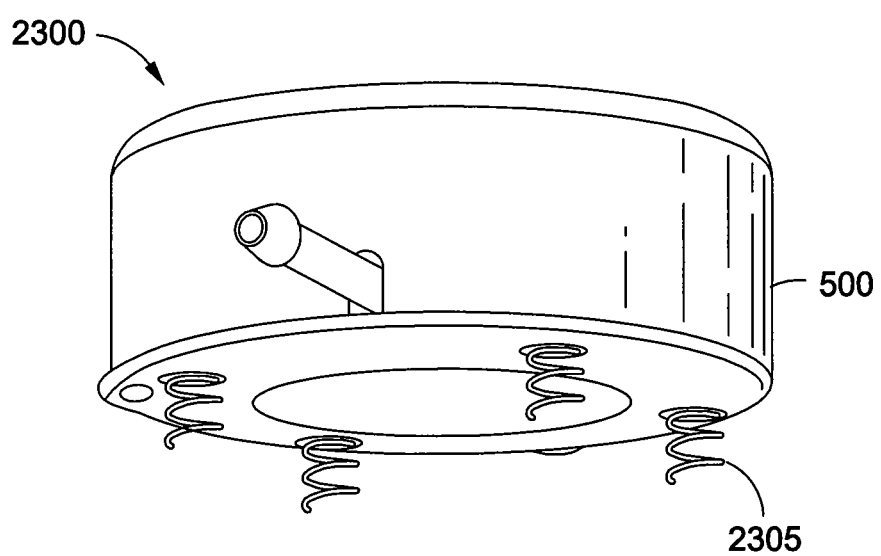

FIGS. 23 and 24 are perspective top and bottom views of a port 2300 having cork screw anchors 2305 according to an embodiment of the invention. The cork screw port 2400 has cork screw anchors 2405 protruding through the base 245 and capable of being screwed into the bodily tissue. The top portion 205 can be rotated causing a rotating device 2310 to rotate with the top portion 205 and move the cork screw anchors 2405 into and out of the housing 500 (i.e., from an un-deployed position to a deployed position and vice versa).

Figure 25:
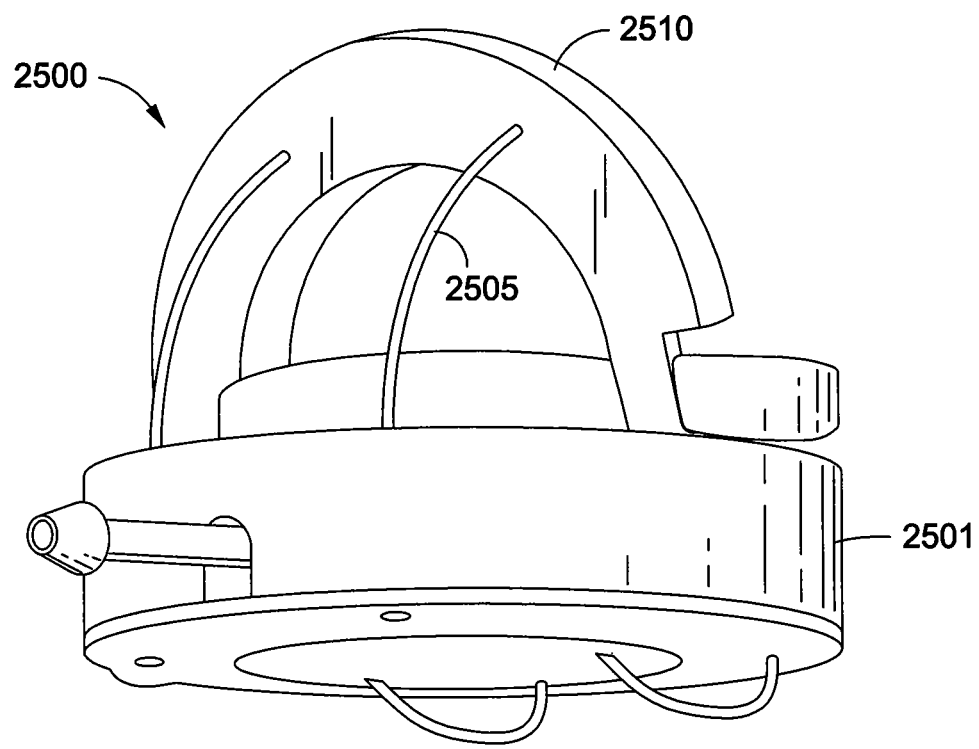
FIG. 25 is a perspective view of a flip top port according to an embodiment of the present invention.
Figure 26:
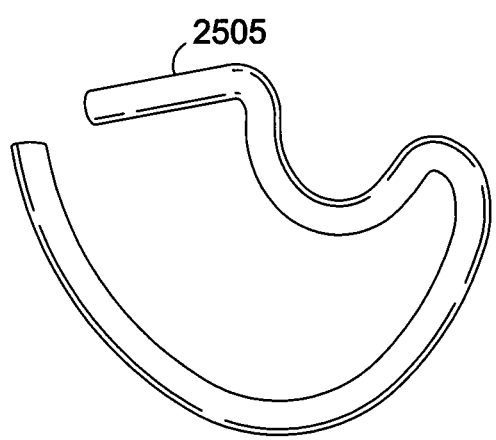
FIG. 26 is a side view of a flip top anchor according to an embodiment of the present invention.

FIG. 25 is a perspective view of a flip top port 2500 according to an embodiment of the present invention. FIG. 26 is a side view of a flip top anchor 2505 according to an embodiment of the present invention. The flip top anchors 2505 attach to bodily tissue as the flip top 2510 is moved downwards. When the flip top 2510 is pulled up, the anchors 2505 are in an undeployed position and when the flip top 2510 is pushed down and comes into contact with the housing 2501, the anchors 2505 in a deployed position.

Figure 27:
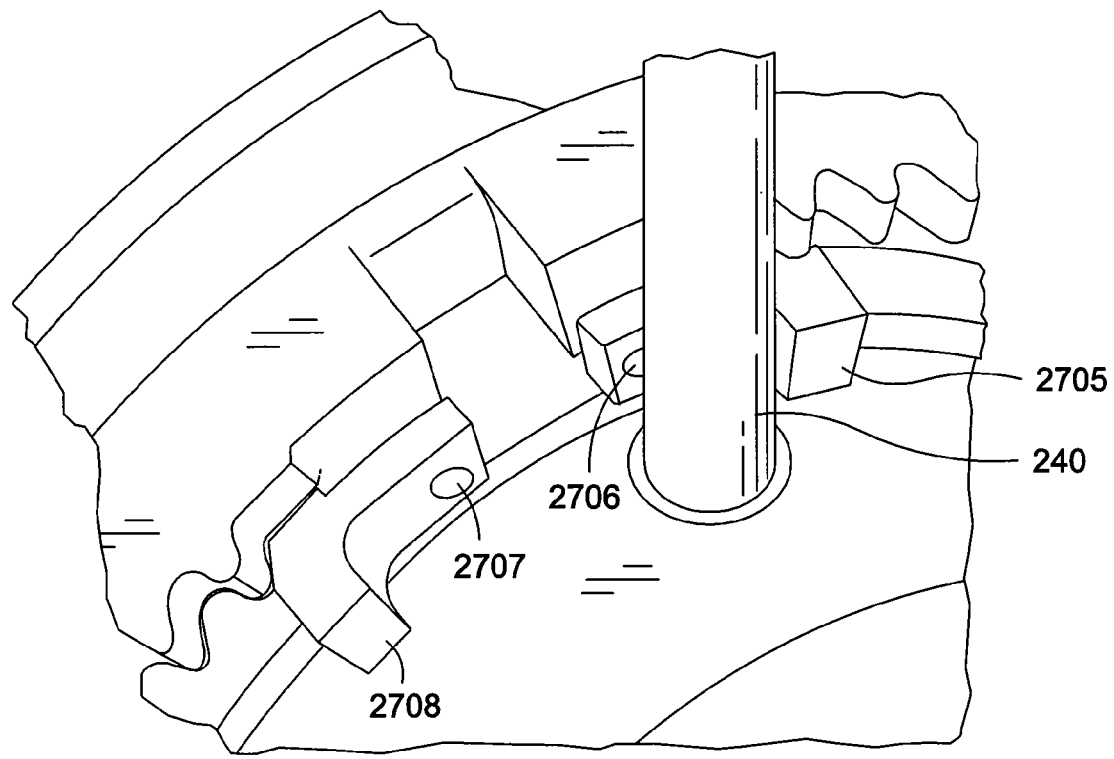
FIGS. 27 and 28 are partial perspective views of a locking rod capable of being locked onto a base of a port according to an embodiment of the present invention.
Figure 28:
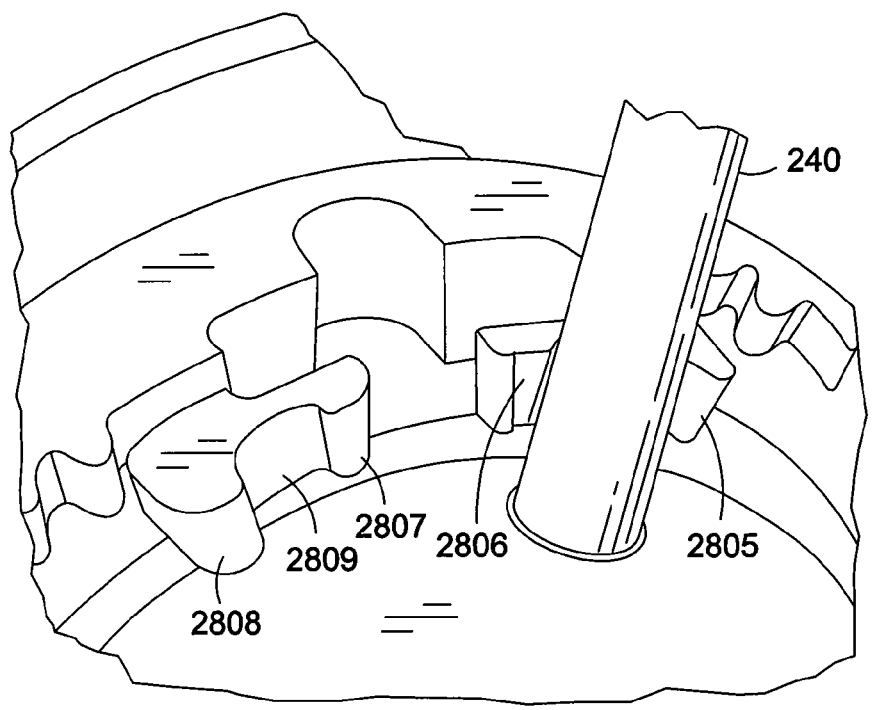

FIGS. 27 and 28 are bottom side views of the stem 240 in a right side position indicating an undeployed position for the anchors according to an embodiment of the present invention. In FIG. 27, the stem 240 is locked in place between a flange 2705 or 2708 and a bump or protrusion 2706 or 2707 on the flange 2705 or 2708. The flanges 2705 and 2708 may be formed in the shape of a "L" and may be attached to the base 245 as shown in FIG. 20. The stem 240 may move between a left side position indicating a deployed position for the anchors and a right side position indicating an undeployed position for the anchors. Each flange 2705 or 2708 may have a cutout 2809 for securing or locking the stem 240 in place. When the stem 240 is in the cutout 2809, the anchors are in a locked position. In FIG. 28, the stem 240 is locked in place between a flange 2805 or 2808 and a bump or protrusion 2806 or 2807 on the flange 2805 or 2808. The flanges 2805 and 2808 may be formed in the shape of a "L" and may be attached to the base 245 as shown in FIG. 20. The stem 240 may move between a left side position indicating a deployed position for the anchors and a right side position indicating an undeployed position for the anchors. Each flange 2805 or 2808 may have a cutout 2809 for securing or locking the stem 240 in place. When the stem 240 is in the cutout 2809, the anchors are in a locked position.

FIGS. 29 and 30 are assembled and disassembled perspective views of the applier 135 according to an embodiment of the present invention. The applier 135 may be used to secure the port 130 to the human 105, as rotation of the applier handle 3005 rotates the top portion 205 of the port 130 and secures the anchors 255 of the port 130 into the human 105. As illustrated, the applier 135 includes a handle 3005, a shaft 3010, a driver or a spring 3015, a sleeve 3020 that holds the shaft 3010 and the driver 3015, and a connector 3025. The handle 3005 is used to place and rotate the applier 135. The shaft 3010 can provide leverage through its length or through internal components. The connector 3025 attaches to the fittings 207 on the top of the top portion 205. The spring 3015 can apply pressure to the driver 3015. The sleeve 3020 covers and protects the shaft 3010 and the spring 3015. The applier 135 mates with the port 130 to turn the gears 275 by turning the top portion 205. A medical professional turns the applier handle 3005 in a large circular direction to turn the top portion 205 of the port 130. The applier 135 may be disposable. Also, the port 130 can be attached to bodily tissue by suturing.

Figure 31:
FIGS. 31 and 32 are perspective views of different appliers and according to various embodiments of the present invention.
Figure 32:
Figure 33:
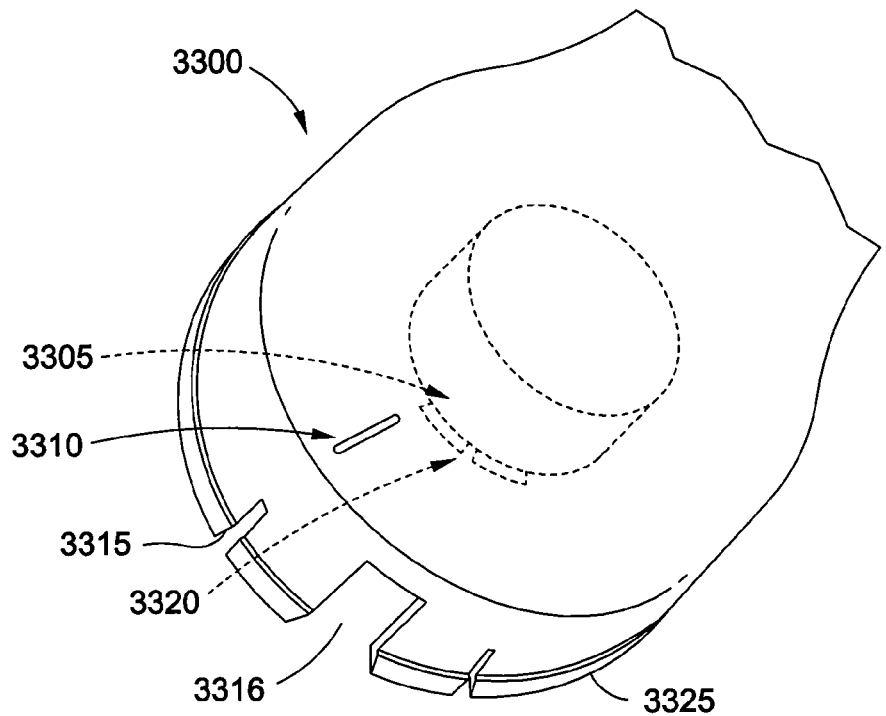
FIG. 33 is an end view of the applier of FIG. 32 according to an embodiment of the present invention.

FIGS. 31 and 32 are perspective views of different appliers 3100 and 3200 according to various embodiments of the present invention. FIG. 33 is an end view of the applier 3200 of FIG. 32 according to an embodiment of the present invention. The end portion 3300 has a cutout 3316 that can attach to or fit around the coupler 501 shown in FIG. 8. Additionally, an inside surface of the end portion 3300 can include protrusions that mate with and attach to the slits 502 and 504 of the housing 500 to allow better attachment and grip to rotate the top portion 205. In one embodiment, the top portion 205 is fixedly attached to the housing 500 so both components rotate together. The end portion 3300 may have a connector 3305 with protrusions 3320 that attach to the fittings 207. The rim 3325 is sized to be larger than the housing 500 so the rim 3325 can fit over the housing 500.

The terms "a," "an," "the," and similar referents used in the context of describing the present invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the present invention otherwise claimed. No language in the specification should be construed as indicating any non-claimed element essential to the practice of the present invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the present invention disclosed herein are illustrative of the principles of the present invention. Other modifications that may be employed are within the scope of the present invention. Thus, by way of example, but not of limitation, alternative configurations of the present invention may be utilized in accordance with the teachings herein. Accordingly, the present invention is not limited to that precisely as shown and described herein.

The previous description of the disclosed examples is provided to enable any person of ordinary skill in the art to make or use the disclosed methods and apparatus. Various modifications to these examples will be readily apparent to those skilled in the art, and the principles defined herein may be applied to other examples without departing from the spirit or scope of the disclosed method and apparatus. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. An implantable injection port for use with a gastric band for treating obesity and for attaching to a tissue of a patient, the implantable injection port comprising:
    a base having an anchor opening;
    a gear coupled to the base and rotatable about a first axis of the gear, the gear having a plurality of gear teeth;
    an anchor coupled to the gear, wherein the anchor has an attachment end coupled to the gear and a free end that is curved; and
    a top portion spaced apart from the base and having a plurality of top teeth that engage with the plurality of gear teeth, the top portion being rotatable about a second axis transverse to the first axis causing rotation of the gear such that the rotation of the gear causes movement of the anchor through the anchor opening of the base and into the tissue of the patient.

2. The implantable injection port of claim 1, wherein the anchor free end is configured in the shape of a hook.

3. The implantable injection port of claim 2, wherein the anchor has a flat surface adjacent to the attachment end that is used to stop the anchor from rotating beyond a predetermined position.

4. The implantable injection port of claim 1, wherein the anchor is formed in the shape of a spiral and has a pointed end.

5. The implantable injection port of claim 1, wherein the top portion has a center opening and an outer portion surrounding the center opening, the outer portion having one or more fittings.

6. The implantable injection port of claim 5, further comprising a septum positioned within the center opening of the top portion and made of a self sealing needle penetrable material.

7. The implantable injection port of claim 6, further comprising a reservoir positioned underneath the septum and between the top portion and the base for holding fluid.

8. The implantable injection port of claim 7, further comprising a stem extending outward from the reservoir and a flange connected to the base and having a first end and a second end, the stem being movable along the flange from the first end to the second end.

9. The implantable injection port of claim 8, wherein the anchor is in a deployed position when the stem is positioned at the first end of the flange and the anchor is in an undeployed position when the stem is positioned at the second end of the flange.

10. The implantable injection port of claim 9, wherein the flange has a plurality of protrusions to lock the stem in place.

11. The implantable injection port of claim 5, further comprising an actuation device having a handle and a port interface that attaches to and detaches from the one or more fittings to rotate the top portion.

12. The implantable injection port of claim 1, wherein the anchor is constructed to rotate about the first axis with the gear.

13. An implantable injection port system for use with a gastric band for treating obesity and for attaching to a tissue of a patient, the implantable injection port system comprising:
    a catheter having a first end and a second end;
    a gastric band attached to the first end of the catheter; and
    a port attached to the second end of the catheter, the port comprising:
        a top portion having top and bottom surfaces and top teeth protruding from the bottom surface, a septum, and one or more fittings on the top surface,
        a base spaced apart from the top portion,
        a gear attached to the base and rotatable about a first axis of the gear, the gear having a plurality of bottom teeth that interact with the top teeth so that rotation of the top portion about a second axis transverse to the first axis causes rotation of the gear, and
        an anchor attached to the gear, wherein rotation of the top portion causes rotation of the gear causing the anchor to move into and out of bodily tissue.

14. The implantable injection port system of claim 13, wherein the port comprises an implantable access port.

15. The implantable injection port system of claim 13, wherein the gastric band and the port are placed subcutaneously inside a patient.

16. The implantable injection port system of claim 13, further comprising an applier configured to rotate the top portion.

17. An implantable injection port for use with a gastric band for treating obesity and for attaching to a tissue of a patient, the implantable injection port comprising:
    a base having an anchor opening;
    a gear coupled to the base and rotatable about a central axis, the gear having a plurality of gear teeth;
    an anchor coupled to the gear and rotatable about the central axis with the gear; and
    a top portion spaced apart from the base and having a plurality of top teeth that engage with the plurality of gear teeth, the top portion being rotatable causing rotation of the gear such that the rotation of the gear causes movement of the anchor through the anchor opening of the base and into the tissue of the patient.

18. An applier apparatus comprising:
a proximal end having a handle to be held by a medical professional or attached to a gripping device for rotating the handle;
a shaft attached to the handle, wherein rotation of the handle rotates the shaft; and
a distal end having a driver configured to mate with a fitting on a port to secure the port to a patient,
wherein the port comprises:
a top portion having an open center portion and a plurality of top teeth,
a base having an anchor opening,
a cylindrical port positioned between the top portion and the base,
a gear coupled to the base and having teeth that engage with the plurality of top teeth, and
an anchor attached to the gear, the top portion being rotatable causing rotation of the anchor about an axis of rotation of the gear such that the anchor passes through the anchor opening, the rotation of the gear causing rotation of the anchor into and out of bodily tissue.

19. The apparatus of claim 18, wherein the applier comprises a compression spring around the shaft.

20. The apparatus of claim 19, wherein the applier comprises a sleeve surrounding the compression spring.

21. The apparatus of claim 18, wherein the anchor is formed in the shape of a cork screw.

* * * * *